(12) United States Patent
Ward

(10) Patent No.: US 10,307,074 B2
(45) Date of Patent: Jun. 4, 2019

(54) MONITORING SYSTEM AND PROBE

(75) Inventor: Leigh Cordwin Ward, Kenmore Hills (AU)

(73) Assignee: IMPEDIMED LIMITED, Pinkenba, Queensland (AU)

(*) Notice: Subject to any disclaimer, the term of this patent is extended or adjusted under 35 U.S.C. 154(b) by 415 days.

(21) Appl. No.: 12/596,833

(22) PCT Filed: Apr. 17, 2008

(86) PCT No.: PCT/AU2008/000539
§ 371 (c)(1),
(2), (4) Date: Feb. 4, 2010

(87) PCT Pub. No.: WO2008/128281
PCT Pub. Date: Oct. 30, 2008

(65) Prior Publication Data
US 2010/0152605 A1    Jun. 17, 2010

(30) Foreign Application Priority Data

Apr. 20, 2007    (AU) ................................ 2007902109

(51) Int. Cl.
*A61B 5/00* (2006.01)
*A61B 5/053* (2006.01)

(52) U.S. Cl.
CPC .......... *A61B 5/0537* (2013.01); *A61B 5/4878* (2013.01); *A61B 2562/0209* (2013.01); *A61B 2562/043* (2013.01)

(58) Field of Classification Search
CPC ..... A61B 5/053; A61B 5/0531; A61B 5/0532; A61B 5/0536; A61B 5/4878; A61B 2562/0209; A61B 2562/043

USPC .......................................................... 600/547
See application file for complete search history.

(56) References Cited

U.S. PATENT DOCUMENTS

| | | | |
|---|---|---|---|
| 3,316,896 A | | 5/1967 | Thomasset |
| 3,834,374 A | * | 9/1974 | Ensanian ...................... 600/397 |
| 3,851,641 A | | 12/1974 | Toole |
| 3,866,600 A | | 2/1975 | Rey |
| 3,868,165 A | | 2/1975 | Gonser |
| 3,871,359 A | | 3/1975 | Pacela |
| 4,008,712 A | | 2/1977 | Nyboer |
| 4,032,889 A | * | 6/1977 | Nassimbene .......... A61B 5/117 250/221 |
| 4,034,854 A | | 7/1977 | Bevilacqua |

(Continued)

FOREIGN PATENT DOCUMENTS

| CA | 2231038 A1 | 11/1999 |
|---|---|---|
| CA | 2613524 A1 | 1/2007 |

(Continued)

OTHER PUBLICATIONS

U.S. Appl. No. 12/302,914, filed Apr. 8, 2010, McGree.

(Continued)

*Primary Examiner* — Max F Hindenburg
(74) *Attorney, Agent, or Firm* — Knobbe, Martens, Olson & Bear, LLP

(57) ABSTRACT

A probe for use in performing impedance measurements on a subject. The probe includes a housing for being held by an operator in use, a contact surface for contacting the subject and a connector for connecting the contact surface to a measuring device.

43 Claims, 10 Drawing Sheets

(56) References Cited

U.S. PATENT DOCUMENTS

| | | |
|---|---|---|
| 4,082,087 A | 4/1978 | Howson |
| 4,121,575 A | 10/1978 | Mills |
| 4,144,878 A | 3/1979 | Wheeler |
| RE30,101 E | 9/1979 | Kubicek et al. |
| 4,169,463 A | 10/1979 | Piquard |
| 4,184,486 A | 1/1980 | Papa |
| 4,233,987 A | 11/1980 | Feingold |
| 4,291,708 A | 9/1981 | Frei et al. |
| 4,314,563 A | 2/1982 | Wheeler |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,638,807 A | 1/1987 | Ryder |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,836,214 A | 6/1989 | Sramek |
| 4,890,630 A | 1/1990 | Kroll et al. |
| 4,895,163 A | 1/1990 | Libke et al. |
| 4,905,705 A | 3/1990 | Kizakevich et al. |
| 4,911,175 A | 3/1990 | Shizgal |
| 4,922,911 A | 5/1990 | Wada |
| 4,924,875 A | 5/1990 | Chamoun |
| 4,942,880 A | 7/1990 | Slovak |
| 4,951,682 A | 8/1990 | Petre |
| 4,981,141 A | 1/1991 | Segalowitz |
| 5,020,541 A | 6/1991 | Marriott |
| 5,025,784 A | 6/1991 | Shao et al. |
| 5,063,937 A | 11/1991 | Ezenwa et al. |
| 5,086,781 A | 2/1992 | Bookspan |
| 5,101,828 A | 4/1992 | Welkowitz et al. |
| 5,143,079 A | 9/1992 | Frei et al. |
| 5,184,624 A | 2/1993 | Brown et al. |
| 5,197,479 A | 3/1993 | Hubelbank et al. |
| 5,233,982 A | 8/1993 | Kohl |
| 5,246,008 A | 9/1993 | Mueller |
| 5,272,624 A | 12/1993 | Gisser et al. |
| 5,280,429 A | 1/1994 | Withers |
| 5,282,840 A | 2/1994 | Hudrlik |
| 5,284,142 A | 2/1994 | Goble et al. |
| 5,305,192 A | 4/1994 | Bonte et al. |
| 5,309,917 A | 5/1994 | Wang et al. |
| 5,311,878 A | 5/1994 | Brown et al. |
| 5,335,667 A | 8/1994 | Cha et al. |
| 5,351,697 A | 10/1994 | Cheney et al. |
| 5,353,802 A | 10/1994 | Ollmar |
| 5,372,141 A | 12/1994 | Gallup et al. |
| 5,381,333 A | 1/1995 | Isaacson et al. |
| 5,390,110 A | 2/1995 | Cheney et al. |
| 5,415,164 A | 5/1995 | Faupel et al. |
| 5,421,344 A | 6/1995 | Popp |
| 5,421,345 A | 6/1995 | Lekholm et al. |
| 5,423,326 A | 6/1995 | Wang et al. |
| 5,427,113 A | 6/1995 | Hiroshi |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A | 4/1996 | Reining |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,575,929 A | 11/1996 | Yu et al. |
| 5,588,429 A | 12/1996 | Isaacson et al. |
| 5,596,283 A * | 1/1997 | Mellitz et al. ............ 324/750.22 |
| 5,611,351 A | 3/1997 | Sato et al. |
| 5,615,689 A | 4/1997 | Kotler |
| 5,626,146 A | 5/1997 | Barber et al. |
| 5,704,355 A | 1/1998 | Bridges |
| 5,718,231 A * | 2/1998 | Dewhurst et al. ............ 600/462 |
| 5,730,136 A | 3/1998 | Laufer |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A | 8/1998 | Feldman |
| 5,800,350 A | 9/1998 | Coppleson et al. |
| 5,807,251 A | 9/1998 | Wang et al. |
| 5,807,270 A | 9/1998 | Williams |
| 5,807,272 A | 9/1998 | Kun et al. |
| 5,810,742 A | 9/1998 | Pearlman |
| 5,876,353 A | 3/1999 | Riff |
| 5,919,142 A | 7/1999 | Boone et al. |
| 5,947,910 A | 9/1999 | Zimmet |
| 5,957,861 A | 9/1999 | Combs et al. |
| 5,964,703 A | 10/1999 | Goodman et al. |
| 5,994,956 A | 11/1999 | Concorso |
| 6,011,992 A | 1/2000 | Hubbard et al. |
| 6,015,389 A | 1/2000 | Brown |
| 6,018,677 A | 1/2000 | Vidrine et al. |
| 6,101,413 A | 8/2000 | Olson |
| 6,115,626 A | 9/2000 | Whayne et al. |
| 6,122,544 A | 9/2000 | Organ |
| 6,125,297 A | 9/2000 | Scionolfi |
| 6,129,666 A | 10/2000 | DeLuca et al. |
| 6,142,949 A | 11/2000 | Ubby |
| 6,151,523 A | 11/2000 | Ferrer et al. |
| 6,167,300 A | 12/2000 | Cherepenin et al. |
| 6,173,003 B1 | 1/2001 | Whikehart et al. |
| 6,208,890 B1 | 3/2001 | Sarrazin et al. |
| 6,228,033 B1 | 5/2001 | Koobi et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,253,100 B1 | 6/2001 | Zhdanov |
| 6,256,532 B1 | 7/2001 | Cha |
| 6,280,396 B1 | 8/2001 | Clark |
| 6,292,690 B1 | 9/2001 | Petrucelli et al. |
| 6,308,097 B1 | 10/2001 | Pearlman |
| 6,339,722 B1 | 1/2002 | Heethaar et al. |
| 6,354,996 B1 | 3/2002 | Drinan et al. |
| 6,376,023 B1 | 4/2002 | Mori |
| 6,432,045 B2 | 8/2002 | Lemperle et al. |
| 6,440,084 B1 * | 8/2002 | Gentempo ............... A61B 5/01 600/549 |
| 6,459,930 B1 | 10/2002 | Takehara et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,501,984 B1 | 12/2002 | Church et al. |
| 6,511,438 B2 | 1/2003 | Bernstein et al. |
| 6,512,949 B1 | 1/2003 | Combs et al. |
| 6,516,218 B1 | 2/2003 | Cheng et al. |
| 6,522,910 B1 | 2/2003 | Gregory |
| 6,532,384 B1 | 3/2003 | Fukuda |
| 6,551,252 B2 | 4/2003 | Sackner et al. |
| 6,556,001 B1 | 4/2003 | Wiegand |
| 6,560,480 B1 | 5/2003 | Nachaliel et al. |
| 6,561,986 B2 | 5/2003 | Baura et al. |
| 6,564,079 B1 | 5/2003 | Cory et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtke |
| 6,633,777 B2 | 10/2003 | Szopinski |
| 6,636,754 B1 | 10/2003 | Baura et al. |

(56) References Cited

U.S. PATENT DOCUMENTS

| | | | |
|---|---|---|---|
| 6,643,543 B2 | 11/2003 | Takehara et al. |
| 6,658,296 B1 | 12/2003 | Wong et al. |
| 6,714,813 B2 | 3/2004 | Ishigooka et al. |
| 6,714,814 B2 | 3/2004 | Yamada |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,753,487 B2 | 6/2004 | Fujii et al. |
| 6,760,617 B2 | 7/2004 | Ward et al. |
| 6,763,263 B2 | 7/2004 | Gregory et al. |
| 6,768,921 B2 | 7/2004 | Organ et al. |
| 6,788,966 B2 | 9/2004 | Kenan et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,840,907 B1 | 1/2005 | Brydon |
| 6,845,264 B1 | 1/2005 | Skladnev et al. |
| 6,870,109 B1 | 3/2005 | Villarreal |
| 6,875,176 B2 | 4/2005 | Mourad |
| 6,906,533 B1 | 6/2005 | Yoshida |
| 6,922,586 B2 | 7/2005 | Davies |
| 6,936,012 B2 | 8/2005 | Wells |
| 6,940,286 B2 | 9/2005 | Wang et al. |
| RE38,879 E | 11/2005 | Goodman et al. |
| 6,980,852 B2 | 12/2005 | Jersey-Willuhn et al. |
| 6,980,853 B2 | 12/2005 | Myoshi |
| 7,065,399 B2 | 6/2006 | Nakada |
| 7,079,889 B2 | 7/2006 | Nakada |
| 7,096,061 B2 | 8/2006 | Arad |
| 7,113,622 B2 * | 9/2006 | Hamid ............... G06K 9/00026 382/115 |
| 7,122,012 B2 | 10/2006 | Bouton et al. |
| 7,130,680 B2 | 10/2006 | Kodama et al. |
| 7,132,611 B2 | 11/2006 | Gregaard |
| 7,148,701 B2 | 12/2006 | Park et al. |
| 7,149,573 B2 | 12/2006 | Wang |
| 7,164,522 B2 | 1/2007 | Kimura et al. |
| 7,169,107 B2 | 1/2007 | Jersey-Willuhn |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,206,630 B1 | 4/2007 | Tarler |
| 7,212,852 B2 | 5/2007 | Smith et al. |
| 7,214,107 B2 | 5/2007 | Powell et al. |
| 7,233,823 B2 | 6/2007 | Simond et al. |
| 7,251,524 B1 | 7/2007 | Hepp et al. |
| 7,270,580 B2 | 9/2007 | Bradley et al. |
| 7,288,943 B2 | 10/2007 | Matthiessen et al. |
| D557,809 S | 12/2007 | Neverov |
| 7,313,435 B2 | 12/2007 | Nakada et al. |
| 7,317,161 B2 | 1/2008 | Fukuda |
| 7,336,992 B2 | 2/2008 | Shiokawa |
| 7,353,058 B2 * | 4/2008 | Weng et al. ................ 600/547 |
| 7,390,303 B2 | 6/2008 | Dafni |
| 7,440,796 B2 | 10/2008 | Woo et al. |
| 7,457,660 B2 | 11/2008 | Smith et al. |
| 7,477,937 B2 | 1/2009 | Iijima et al. |
| 7,496,450 B2 | 2/2009 | Ortiz Aleman et al. |
| 7,499,745 B2 * | 3/2009 | Littrup et al. ................ 600/547 |
| D603,051 S | 10/2009 | Causevic |
| 7,603,158 B2 | 10/2009 | Nachman |
| 7,603,171 B2 | 10/2009 | Eror et al. |
| 7,628,761 B2 | 12/2009 | Gozani et al. |
| 7,638,341 B2 | 12/2009 | Rubinsky et al. |
| 7,657,292 B2 | 2/2010 | Baker, Jr. |
| 7,660,617 B2 | 2/2010 | Davis |
| 7,706,872 B2 | 4/2010 | Min et al. |
| 7,711,418 B2 | 5/2010 | Garber et al. |
| 7,729,756 B2 | 6/2010 | Mertelmeier et al. |
| 7,733,224 B2 | 6/2010 | Tran |
| 7,860,557 B2 | 12/2010 | Istvan |
| 7,917,202 B2 | 3/2011 | Chamney et al. |
| D641,886 S | 7/2011 | Causevic |
| 7,983,853 B2 | 7/2011 | Wang et al. |
| D647,208 S | 10/2011 | Rothman |
| 8,055,335 B2 | 11/2011 | Stylos |
| 8,068,906 B2 | 11/2011 | Chetham |
| 8,172,762 B2 | 5/2012 | Robertson |
| 8,233,617 B2 | 7/2012 | Johnson |
| 8,233,974 B2 | 7/2012 | Ward |
| D669,186 S | 10/2012 | Gozani |
| D669,187 S | 10/2012 | Gozani |
| 8,285,356 B2 | 10/2012 | Bly et al. |
| D674,096 S | 1/2013 | Gaw |
| 8,467,865 B2 | 6/2013 | Gregory |
| 8,744,564 B2 | 6/2014 | Ward et al. |
| D718,458 S | 11/2014 | Vosch |
| D719,660 S | 12/2014 | Vosch |
| D728,801 S | 5/2015 | Machon |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0021799 A1 | 9/2001 | Ohlsson |
| 2001/0025139 A1 | 9/2001 | Pearlman |
| 2001/0051774 A1 | 12/2001 | Littrup |
| 2002/0022773 A1 | 2/2002 | Drinan |
| 2002/0022787 A1 | 2/2002 | Takehara et al. |
| 2002/0035334 A1 | 3/2002 | Meij |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0106681 A1 | 8/2002 | Wexler |
| 2002/0109621 A1 | 8/2002 | Khair et al. |
| 2002/0111559 A1 | 8/2002 | Kurata |
| 2002/0123694 A1 | 9/2002 | Organ et al. |
| 2002/0138019 A1 | 9/2002 | Wexler |
| 2002/0161311 A1 | 10/2002 | Ward et al. |
| 2002/0163408 A1 | 11/2002 | Fujii et al. |
| 2002/0194419 A1 | 12/2002 | Rajput et al. |
| 2003/0004403 A1 | 1/2003 | Drinan |
| 2003/0009111 A1 | 1/2003 | Cory |
| 2003/0023184 A1 | 1/2003 | Pitts-Crick et al. |
| 2003/0028221 A1 | 2/2003 | Zhu et al. |
| 2003/0036713 A1 | 2/2003 | Bouton |
| 2003/0050570 A1 | 3/2003 | Kodama |
| 2003/0068914 A1 | 4/2003 | Merry et al. |
| 2003/0073916 A1 | 4/2003 | Yonce |
| 2003/0105410 A1 | 6/2003 | Pearlman |
| 2003/0105411 A1 * | 6/2003 | Smallwood et al. ......... 600/547 |
| 2003/0120170 A1 | 6/2003 | Zhu et al. |
| 2003/0120182 A1 | 6/2003 | Wilkinson et al. |
| 2003/0173976 A1 | 9/2003 | Wiegand |
| 2003/0176808 A1 | 9/2003 | Masuo |
| 2003/0216661 A1 | 11/2003 | Davies |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0059220 A1 | 3/2004 | Mourad |
| 2004/0073127 A1 | 4/2004 | Istvan et al. |
| 2004/0073130 A1 | 4/2004 | Bohm |
| 2004/0077944 A1 | 4/2004 | Steinberg et al. |
| 2004/0116819 A1 | 6/2004 | Alt |
| 2004/0127793 A1 | 7/2004 | Mendlein |
| 2004/0158167 A1 | 8/2004 | Smith et al. |
| 2004/0167423 A1 | 8/2004 | Pillon et al. |
| 2004/0171691 A1 | 9/2004 | Smith |
| 2004/0181163 A1 | 9/2004 | Acumen |
| 2004/0181164 A1 | 9/2004 | Smith et al. |
| 2004/0186392 A1 | 9/2004 | Ward et al. |
| 2004/0204658 A1 * | 10/2004 | Dietz et al. ................... 600/547 |
| 2004/0210150 A1 | 10/2004 | Virtanen |
| 2004/0210158 A1 | 10/2004 | Organ et al. |
| 2004/0220632 A1 | 11/2004 | Burnes |
| 2004/0234113 A1 | 11/2004 | Miga |
| 2004/0236202 A1 | 11/2004 | Burton |
| 2004/0242987 A1 | 12/2004 | Liew |
| 2004/0242989 A1 | 12/2004 | Zhu |
| 2004/0243018 A1 | 12/2004 | Organ et al. |
| 2004/0252870 A1 | 12/2004 | Reeves et al. |
| 2004/0253652 A1 | 12/2004 | Davies |
| 2004/0260167 A1 | 12/2004 | Leonhardt |
| 2004/0267333 A1 | 12/2004 | Kronberg |
| 2004/0267344 A1 | 12/2004 | Stett et al. |

(56) References Cited

U.S. PATENT DOCUMENTS

| | | |
|---|---|---|
| 2005/0033281 A1 | 2/2005 | Bowman et al. |
| 2005/0039763 A1 | 2/2005 | Kraemer et al. |
| 2005/0070778 A1 | 3/2005 | Lackey et al. |
| 2005/0080460 A1 | 4/2005 | Wang |
| 2005/0085743 A1 | 4/2005 | Hacker et al. |
| 2005/0098343 A1 | 5/2005 | Fukuda |
| 2005/0101875 A1 | 5/2005 | Semler et al. |
| 2005/0107719 A1 | 5/2005 | Arad (Abbound) et al. |
| 2005/0113704 A1 | 5/2005 | Lawson et al. |
| 2005/0117196 A1 | 6/2005 | Kimura et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177061 A1 | 8/2005 | Alanen et al. |
| 2005/0177062 A1 | 8/2005 | Skrabal et al. |
| 2005/0192488 A1 | 9/2005 | Bryenton et al. |
| 2005/0201598 A1 | 9/2005 | Harel |
| 2005/0203435 A1 | 9/2005 | Nakada |
| 2005/0203436 A1 | 9/2005 | Davies |
| 2005/0215918 A1 | 9/2005 | Frantz |
| 2005/0228309 A1 | 10/2005 | Fisher |
| 2005/0251062 A1 | 11/2005 | Choi |
| 2005/0261743 A1 | 11/2005 | Kroll |
| 2005/0270051 A1 | 12/2005 | Yee et al. |
| 2005/0283091 A1 | 12/2005 | Kink et al. |
| 2006/0004300 A1 | 1/2006 | Kennedy |
| 2006/0025701 A1 | 2/2006 | Kasahara |
| 2006/0041280 A1 | 2/2006 | Stahmann et al. |
| 2006/0041789 A1 | 3/2006 | Takehara |
| 2006/0052678 A1 | 3/2006 | Drinan |
| 2006/0064029 A1 | 3/2006 | Arad (Abboud) |
| 2006/0070623 A1 | 4/2006 | Wilkinson |
| 2006/0085048 A1 | 4/2006 | Cory et al. |
| 2006/0085049 A1 | 4/2006 | Cory et al. |
| 2006/0100532 A1 | 5/2006 | Bae |
| 2006/0110962 A1 | 5/2006 | Powell et al. |
| 2006/0111652 A1 | 5/2006 | McLeod |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0128193 A1 | 6/2006 | Bradley et al. |
| 2006/0135886 A1 | 6/2006 | Lippert et al. |
| 2006/0151815 A1 | 7/2006 | Graovac et al. |
| 2006/0184060 A1 | 8/2006 | Belalcazar |
| 2006/0197509 A1 | 9/2006 | Kanamori et al. |
| 2006/0200033 A1 | 9/2006 | Keren et al. |
| 2006/0224079 A1 | 10/2006 | Washchuk |
| 2006/0224080 A1 | 10/2006 | Oku et al. |
| 2006/0241513 A1 | 10/2006 | Hatlestad et al. |
| 2006/0241719 A1 | 10/2006 | Foster |
| 2006/0247543 A1 | 11/2006 | Cornish |
| 2006/0252670 A1 | 11/2006 | Fiorucci |
| 2006/0253016 A1 | 11/2006 | Baker |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | Mcadams |
| 2006/0293609 A1 | 12/2006 | Stahmann et al. |
| 2007/0007975 A1 | 1/2007 | Hawkins |
| 2007/0010758 A1 | 1/2007 | Matthiessen et al. |
| 2007/0024310 A1 | 2/2007 | Tokuno et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0088227 A1 | 4/2007 | Nishimura |
| 2007/0106342 A1 | 5/2007 | Schumann |
| 2007/0118027 A1 | 5/2007 | Baker, Jr. |
| 2007/0156061 A1 | 7/2007 | Hess |
| 2007/0188219 A1 | 8/2007 | Segarra |
| 2007/0246046 A1 | 10/2007 | Teschner et al. |
| 2007/0270707 A1 | 11/2007 | Belalcazar |
| 2008/0001608 A1 | 1/2008 | Saulnier |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0027350 A1 | 1/2008 | Webler |
| 2008/0039700 A1 | 2/2008 | Drinan et al. |
| 2008/0048786 A1 | 2/2008 | Feldkamp |
| 2008/0051643 A1 | 2/2008 | Park et al. |
| 2008/0064981 A1 | 3/2008 | Gregory |
| 2008/0091114 A1 | 4/2008 | Min |
| 2008/0139957 A1 | 6/2008 | Hubbard et al. |
| 2008/0183098 A1 | 7/2008 | Denison |
| 2008/0200802 A1 | 8/2008 | Bhavaraju et al. |
| 2008/0205717 A1 | 8/2008 | Reeves et al. |
| 2008/0221411 A1 | 9/2008 | Hausmann |
| 2008/0247502 A1 | 10/2008 | Liao |
| 2008/0252304 A1 | 10/2008 | Woo et al. |
| 2008/0262375 A1 | 10/2008 | Brown |
| 2008/0270051 A1 | 10/2008 | Essex et al. |
| 2008/0287823 A1 | 11/2008 | Chetham |
| 2008/0306400 A1 | 12/2008 | Takehara |
| 2008/0319336 A1 | 12/2008 | Ward et al. |
| 2009/0018432 A1 | 1/2009 | He |
| 2009/0043222 A1 | 2/2009 | Chetham |
| 2009/0069708 A1 | 3/2009 | Hatlestad et al. |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0076410 A1 | 3/2009 | Libbus et al. |
| 2009/0082679 A1 | 3/2009 | Chetham |
| 2009/0084674 A1 | 4/2009 | Holzhacker et al. |
| 2009/0093730 A1 | 4/2009 | Grassl |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0209828 A1 | 8/2009 | Musin |
| 2009/0209872 A1 | 8/2009 | Pop |
| 2009/0216140 A1 | 8/2009 | Skrabal |
| 2009/0216148 A1 | 8/2009 | Freed |
| 2009/0234244 A1 | 9/2009 | Tanaka |
| 2009/0240163 A1 | 9/2009 | Webler |
| 2009/0264727 A1 | 10/2009 | Markowitz |
| 2009/0264745 A1 | 10/2009 | Markowitz |
| 2009/0264776 A1 | 10/2009 | Vardy |
| 2009/0264791 A1 | 10/2009 | Gregory |
| 2009/0275854 A1 | 11/2009 | Zielinski |
| 2009/0275855 A1 | 11/2009 | Zielinski |
| 2009/0287102 A1 | 11/2009 | Ward |
| 2009/0306535 A1 | 12/2009 | Davies |
| 2009/0318778 A1 | 12/2009 | Dacso et al. |
| 2009/0326408 A1 | 12/2009 | Moon |
| 2010/0007357 A1 | 1/2010 | Ammari et al. |
| 2010/0049077 A1 | 2/2010 | Sadleir |
| 2010/0056881 A1 | 3/2010 | Libbus et al. |
| 2010/0094160 A1 | 4/2010 | Eror et al. |
| 2010/0100003 A1 | 4/2010 | Chetham et al. |
| 2010/0100146 A1 | 4/2010 | Blomqvist |
| 2010/0106046 A1 | 4/2010 | Shochat |
| 2010/0109739 A1 | 5/2010 | Ironstone et al. |
| 2010/0145164 A1 | 6/2010 | Howell |
| 2010/0152605 A1 | 6/2010 | Ward |
| 2010/0168530 A1 | 7/2010 | Chetham et al. |
| 2010/0191141 A1 | 7/2010 | Aberg |
| 2010/0228143 A1 | 9/2010 | Teschner et al. |
| 2010/0234701 A1 | 9/2010 | Cho et al. |
| 2011/0025348 A1 | 2/2011 | Chetham |
| 2011/0034806 A1 | 2/2011 | Hartov et al. |
| 2011/0046505 A1 | 2/2011 | Cornish et al. |
| 2011/0054343 A1 | 3/2011 | Chetham |
| 2011/0054344 A1 | 3/2011 | Slizynski |
| 2011/0060239 A1 | 3/2011 | Gaw |
| 2011/0060241 A1 | 3/2011 | Martinsen et al. |
| 2011/0082383 A1 | 4/2011 | Cory et al. |
| 2011/0087129 A1 | 4/2011 | Chetham |
| 2011/0118619 A1 | 5/2011 | Burton et al. |
| 2011/0190655 A1 | 8/2011 | Moissl |
| 2011/0208084 A1 | 8/2011 | Seoane Martinez |
| 2011/0230784 A2 | 9/2011 | Slizynski |
| 2011/0245712 A1 | 10/2011 | Patterson |
| 2011/0251513 A1 | 10/2011 | Chetham |
| 2011/0274327 A1 | 11/2011 | Wehnes et al. |

(56) References Cited

U.S. PATENT DOCUMENTS

| | | |
|---|---|---|
| 2011/0282180 A1 | 11/2011 | Goldkuhl et al. |
| 2012/0071772 A1 | 3/2012 | Chetham |
| 2012/0165884 A1 | 6/2012 | Xi |
| 2012/0238896 A1 | 9/2012 | Garber et al. |
| 2013/0102873 A1 | 4/2013 | Hamaguchi |
| 2013/0165760 A1 | 6/2013 | Erlinger et al. |
| 2013/0165761 A1 | 6/2013 | De Limon et al. |
| 2014/0148721 A1 | 5/2014 | Erlinger |
| 2014/0371566 A1 | 12/2014 | Raymond et al. |

FOREIGN PATENT DOCUMENTS

| | | | |
|---|---|---|---|
| CA | 2615845 A1 | 1/2007 | |
| CA | 2638958 | 11/2011 | |
| CN | 1180513 A | 5/1998 | |
| CN | 1236597 A | 12/1999 | |
| CN | 1329875 A | 1/2002 | |
| CN | 1366694 A | 8/2002 | |
| CN | 101385203 A | 3/2009 | |
| DE | 2912349 A1 | 10/1980 | |
| EP | 249823 A1 | 12/1987 | |
| EP | 0 339 471 A2 | 11/1989 | |
| EP | 339471 A2 | 11/1989 | |
| EP | 349043 A2 | 1/1990 | |
| EP | 357309 A2 | 3/1990 | |
| EP | 377887 A1 | 7/1990 | |
| EP | 0 581 073 A2 | 2/1994 | |
| EP | 581073 A2 | 2/1994 | |
| EP | 662311 A1 | 7/1995 | |
| EP | 0 865 763 A2 | 9/1998 | |
| EP | 865763 | 9/1998 | |
| EP | 869360 A2 | 10/1998 | |
| EP | 1 078 597 A2 | 2/2001 | |
| EP | 1078597 A2 | 2/2001 | |
| EP | 1 080 686 A1 | 3/2001 | |
| EP | 1080686 A1 | 3/2001 | |
| EP | 1 112 715 A1 | 7/2001 | |
| EP | 1 118 308 A1 | 7/2001 | |
| EP | 1112715 A1 | 7/2001 | |
| EP | 1114610 A1 | 7/2001 | |
| EP | 1146344 A1 | 10/2001 | |
| EP | 1177760 A1 | 2/2002 | |
| EP | 1219937 A1 | 7/2002 | |
| EP | 1238630 A2 | 9/2002 | |
| EP | 1 247 487 A1 | 10/2002 | |
| EP | 1247487 A1 | 10/2002 | |
| EP | 1283539 A1 | 2/2003 | |
| EP | 1 329 190 A1 | 7/2003 | |
| EP | 1329190 A1 | 7/2003 | |
| EP | 1338246 A1 | 8/2003 | |
| EP | 1452131 A1 | 9/2004 | |
| EP | 1553871 A1 | 7/2005 | |
| EP | 1629772 | 3/2006 | |
| EP | 1903938 A1 | 4/2008 | |
| EP | 1909642 A1 | 4/2008 | |
| EP | 1948017 A1 | 7/2008 | |
| EP | 1 353 595 B1 | 8/2008 | |
| FR | 2486386 A1 | 1/1982 | |
| FR | 2748928 A1 | 11/1997 | |
| GB | 1441622 A | 7/1976 | |
| GB | 2131558 A | 6/1984 | |
| GB | 2260416 A | 4/1993 | |
| GB | 2426824 A1 | 12/2006 | |
| IT | 20080030 A1 | 1/2010 | |
| JP | 04-096733 A | 3/1992 | |
| JP | 06-000168 A | 1/1994 | |
| JP | H0674103 U | 10/1994 | |
| JP | 8191808 A | 7/1996 | |
| JP | 9051884 A | 2/1997 | |
| JP | 9220209 A | 8/1997 | |
| JP | 10000185 | 1/1998 | |
| JP | 10014898 A | 1/1998 | |
| JP | 10014899 A | 1/1998 | |
| JP | 10-080406 A | 3/1998 | |
| JP | 10-225521 A | 8/1998 | |
| JP | 11070090 A | 3/1999 | |
| JP | 11-513592 | 11/1999 | |
| JP | 2000107138 A | 4/2000 | |
| JP | 2000139867 A | 5/2000 | |
| JP | 2001037735 A | 2/2001 | |
| JP | 2001-070273 A | 3/2001 | |
| JP | 2001061804 A | 3/2001 | |
| JP | 2001-224568 A | 8/2001 | |
| JP | 2001245866 A | 9/2001 | |
| JP | 2001204707 A | 10/2001 | |
| JP | 2001321352 A | 11/2001 | |
| JP | 2002-350477 | 4/2002 | |
| JP | 2002-238870 A | 8/2002 | |
| JP | 2002330938 A | 11/2002 | |
| JP | 2003116803 A | 4/2003 | |
| JP | 2003116805 A | 4/2003 | |
| JP | 2003-230547 A | 8/2003 | |
| JP | 2003-075487 | 12/2003 | |
| JP | 2004-61251 A | 2/2004 | |
| JP | 2005099186 A | 4/2005 | |
| JP | 2005-143786 A | 6/2005 | |
| JP | 2008022995 A | 2/2008 | |
| RU | 2112416 C1 | 6/1998 | |
| RU | 2138193 C1 | 9/1999 | |
| SU | 1132911 A1 | 1/1985 | |
| WO | 1988007392 A1 | 10/1988 | |
| WO | 91/19454 A1 | 12/1991 | |
| WO | 93/18821 A1 | 9/1993 | |
| WO | 199318821 A1 | 9/1993 | |
| WO | 1993018821 A1 | 9/1993 | |
| WO | 9401040 A1 | 1/1994 | |
| WO | 94/10922 A1 | 5/1994 | |
| WO | 96/01586 A1 | 1/1996 | |
| WO | 199601586 A1 | 1/1996 | |
| WO | 1996001586 A1 | 1/1996 | |
| WO | 1996012439 A1 | 5/1996 | |
| WO | 1996032652 A1 | 10/1996 | |
| WO | 97/11638 A2 | 4/1997 | |
| WO | 1997/011638 | 4/1997 | |
| WO | 1997014358 A1 | 4/1997 | |
| WO | 97/24156 A1 | 7/1997 | |
| WO | 98/06328 A1 | 2/1998 | |
| WO | 199806328 A1 | 2/1998 | |
| WO | 1998006328 A1 | 2/1998 | |
| WO | 9812983 A1 | 4/1998 | |
| WO | 1998/023204 | 6/1998 | |
| WO | 98/33553 A1 | 8/1998 | |
| WO | 1998/033553 | 8/1998 | |
| WO | 98/51211 A1 | 11/1998 | |
| WO | 1998051211 A1 | 11/1998 | |
| WO | 99/42034 A2 | 8/1999 | |
| WO | 99/48422 A1 | 9/1999 | |
| WO | 00/19886 A1 | 4/2000 | |
| WO | 2000/040955 | 7/2000 | |
| WO | 00/78213 A2 | 12/2000 | |
| WO | 2000079255 A1 | 12/2000 | |
| WO | 01/27605 A1 | 4/2001 | |
| WO | 2001027605 A1 | 4/2001 | |
| WO | 01/52733 A1 | 7/2001 | |
| WO | 2001/050954 | 7/2001 | |
| WO | 2001/067098 | 9/2001 | |
| WO | 01/78831 A2 | 10/2001 | |
| WO | 2001082323 A1 | 11/2001 | |
| WO | 2002/047548 A1 | 6/2002 | |
| WO | 02/053028 A2 | 7/2002 | |
| WO | 2002-053028 A2 | 7/2002 | |
| WO | 2002062214 A1 | 8/2002 | |
| WO | 2002094096 A1 | 11/2002 | |
| WO | 2002/100267 A1 | 12/2002 | |
| WO | 2004000115 A1 | 12/2003 | |
| WO | 2004002301 A2 | 1/2004 | |
| WO | 2004006660 A1 | 1/2004 | |
| WO | 2004/021880 A1 | 3/2004 | |
| WO | 2004/030535 A1 | 4/2004 | |
| WO | 2004-032738 A1 | 4/2004 | |
| WO | 2004026136 A1 | 4/2004 | |
| WO | 2004030535 A1 | 4/2004 | |
| WO | 2004032738 A1 | 4/2004 | |
| WO | 2004-043252 A1 | 5/2004 | |

(56) References Cited

FOREIGN PATENT DOCUMENTS

| WO | 2004/047635 | 6/2004 |
|---|---|---|
| WO | 2004/047636 | 6/2004 |
| WO | 2004-047636 A1 | 6/2004 |
| WO | 2004/047638 A1 | 6/2004 |
| WO | 2004/048983 | 6/2004 |
| WO | 2004047638 A1 | 6/2004 |
| WO | 2004049936 A2 | 6/2004 |
| WO | 2004/084087 A1 | 9/2004 |
| WO | 2004083804 A2 | 9/2004 |
| WO | 2004/084723 | 10/2004 |
| WO | 2004/084723 A1 | 10/2004 |
| WO | 2004/084724 | 10/2004 |
| WO | 2004-098389 A2 | 11/2004 |
| WO | 2004112563 A2 | 12/2004 |
| WO | 2005010640 A2 | 2/2005 |
| WO | 2005/027717 | 3/2005 |
| WO | 2005018432 A2 | 3/2005 |
| WO | 2005/051163 A2 | 6/2005 |
| WO | 2005/051194 | 6/2005 |
| WO | 2005/084539 | 9/2005 |
| WO | 2005/122881 A1 | 12/2005 |
| WO | 2005122881 A1 | 12/2005 |
| WO | 2005122888 A1 | 12/2005 |
| WO | 2006/045051 A1 | 4/2006 |
| WO | 2006/056074 A1 | 6/2006 |
| WO | 2006129108 A1 | 12/2006 |
| WO | 2006129116 A1 | 12/2006 |
| WO | 2007002991 A1 | 1/2007 |
| WO | 2007002992 A1 | 1/2007 |
| WO | 2007002993 A1 | 1/2007 |
| WO | 2007009183 A1 | 1/2007 |
| WO | WO 2007/002991 A1 * | 1/2007 |
| WO | 2007/014417 | 2/2007 |
| WO | 2007/041783 | 4/2007 |
| WO | 2007045006 A1 | 4/2007 |
| WO | 2007-056493 A1 | 5/2007 |
| WO | 2007/070997 A1 | 6/2007 |
| WO | 2007089278 A1 | 8/2007 |
| WO | 2007105996 A1 | 9/2007 |
| WO | 2007/128952 A1 | 11/2007 |
| WO | 2008/011716 A1 | 1/2008 |
| WO | 2008064426 A1 | 6/2008 |
| WO | 2008/119166 | 10/2008 |
| WO | 2008119166 A1 | 10/2008 |
| WO | 2008138062 A1 | 11/2008 |
| WO | 2008149125 A1 | 12/2008 |
| WO | 2009/018620 A1 | 2/2009 |
| WO | 2009/027812 A2 | 3/2009 |
| WO | 2009036369 A1 | 3/2009 |
| WO | 2009/059351 | 5/2009 |
| WO | 2009/068961 A2 | 6/2009 |
| WO | 2009/100491 | 8/2009 |
| WO | 2009100491 A1 | 8/2009 |
| WO | 2009/112965 A1 | 9/2009 |
| WO | 2010/003162 A1 | 1/2010 |
| WO | 2010/029465 A2 | 3/2010 |
| WO | 2010/051600 | 5/2010 |
| WO | 2010/060152 | 6/2010 |
| WO | 2010/069023 A2 | 6/2010 |
| WO | 2010/076719 A1 | 7/2010 |
| WO | 2011/018744 A1 | 2/2011 |
| WO | 2011022068 A1 | 2/2011 |
| WO | 2011050393 A1 | 5/2011 |
| WO | 2011075769 A1 | 6/2011 |
| WO | 2011/113169 A1 | 9/2011 |
| WO | 2011/136867 A1 | 11/2011 |
| WO | 2014/176420 A1 | 10/2014 |

OTHER PUBLICATIONS

U.S. Appl. No. 12/516,876, filed Jul. 1, 2010, Chetham.
U.S. Appl. No. 12/600,224, Chetham.
U.S. Appl. No. 12/672,893, filed Feb. 24, 2011, Cornish.
U.S. Appl. No. 10/029,015, filed Oct. 31, 2002, Ward, U.S. Pat. No. 6,760,617.
U.S. Appl. No. 10/767,825, filed Sep. 23, 2004, Ward.
Forslund et al., Evaluation of modified multicompartment models to calculate body composition in healthy males, Am. J. of Clin. Nutrition, 1996; 63:856-62.
Van Loan et al., Use of bioelectrical impedance spectroscopy (BIS) to measure fluid changes during pregnancy, J. Appl. Physiol., 1995; 78:1037-42.
De Lorenzo et al., Predicting body cell mass with bioimpedance by using theoretical methods: a technological review, J. Appl. Physiol., 1997; 82(5):1542-58.
Zhu et al., Segment-specific resistivity improves body fluid volume estimates from bioimpedance spectroscopy in hemodialysis patients, J. Appl. Physiol., Oct 27, 2005; 100:717-24.
Thomas et al., Bioimpedance Spectrometry in the Determination of Body Water Compartments: Accuracy and Clinical Significance, Applied Radiation and Isotopes, 1998; 49(5/6):447-455, Elsevier Science Ltd., Oxford, GB.
Cornish et al., Data analysis in multiple-frequency bioelectrical impedance analysis, Physiological Measurement, 1998; 19(2):275-283, Institute of Physics Publishing, Bristol, GB.
Ulgen et al., Electrical Parameters of Human Blood, Proc. of the 20th Annual Int'l Conference of the IEEE Engineering in Medicine and Biology Soc., 1998; 20(6):2983-2986, IEEE Piscataway, NJ.
Bracco et al., Bedside determination of fluid accumulation after cardiac surgery usign segmental bioelectrical impedance, 1998, Critical Care Medicine, vol. 26 No. 6, pp. 1065-1070.
Chiolero et al., Assessmetn of changes in body water by bioimpedance in acutely ill surgical patients, 1992, Intensive Care Medicine, vol. 18, pp. 322-326.
Chumlea et al., Bioelectrical impedance and body composition: present status and future directions, 1994 Nutrition Reviews, vol. 52, No. 4, pp. 123-131.
Cornish et al., Bioelectrical impedance for monitoring the efficacy of lymphoedema treatment programmes, 1996, Breast Cancer Research and Treatment, vol. 38, pp. 169-176.
Cornish et al., Quantification of lymphoedema using multi-frequency bioimpedance, 1998, Applied Radiation and Isotopes, vol. 49 No. 5/6, pp. 651-652.
De Luca et al., Use of low-frequency electrical impedance mesurements to determine phospholipid content in amniotic fluid, 1996, Physics in Medicine and Biology, vol. 41, pp. 1863-1869.
Derwent Abstract No. 97-474414, JP 09 220209 A (Sekisui Chem Ind Co Ltd) Aug. 26, 1997, see abstract.
Derwent Abstract No. 99-138541, JP 10 014898 A (Sekisui Chem Ind Co Ltd) Jan. 20, 1998, see abstract.
Derwent Abstract No. 99-138542, JP 10 014899 A (Sekisui Chem Ind Co Ltd) Feb. 20, 1998, see abstract.
Derwent Abstract No. 99-247542, JP 11 070090 A (Sekisui Chem Ind Co Ltd) Mar. 16, 1999, see abstract.
Duerenberg et al., Multi-frequency bioelectrical impedance: a comparison between the Cole-Cole modelling and Hanai equations with the classical impedance index approach, 1996, Annals of Human Biology, vol. 23, No. 1, pp. 31-40.
Kim et al., Bioelectrical impedance changes in regional extracellular fluid alterations, 1997, Electromyography and Clinical Neurophysiology, vol. 37, pp. 297-304.
Rigaud et al., Biolectrical impedance techniques in medicine, 1996, Critical Reviews in Biomedical Engineering, vol. 24 (4-6), pp. 257-351.
Steijaert et al., The use of multi-frequency impedance to determine total body water and extracellular water in obese and lean female individuals, 1997, International Journal of Obesity, vol. 21, pp. 930-934.
Ward et al., Multi-frequency bioelectrical impedance augments the diagnosis and management of lymphoedema in post-mastectomy, 1992, European Journal of Clinical Investigation, vol. 22, pp. 751-754.
Liu et al., Primary multi-frequency data analyze in electrical impedance scanning, Proceedings of the IEEE-EMBS 2005, 27th Annual Int'l Conference of the Engineering in Med. and Biology Soc., Shanghai, China, Sep. 4, 2005; 1504-1507.

(56) References Cited

OTHER PUBLICATIONS

Gudivaka et al., Single- and multifrequency models for bioelectrical impedance analysis of body water compartments, J. Appl. Physiol., 1999; 87(3):1087-96.
Gerth et al., A Computer-based Bioelectrical Impedance Spectroscopic System for Noninvasive Assessment of Compartmental Fluid Redistribution, Third Annual IEEE Symposium on Computer-Based Medical Systems Track 6: Clinical Assessment and Risk Evaluation/ Session 13, 1990; 446-453.
Kanai et al., Electrical measurement of fluid distribution in legs and arms, Dept. of Electrical Engineering, Sophia University, 1987; Medical Progress through Technology 12: 159-170, Copyright Martinus Nijhoff Publishers, Boston, MA USA.
European Search Report for EP 07718972.8-1265 / 2020918 (Impedimed, Ltd.), dated Mar. 2, 2010, 4 pages.
Brown et al.; Relation between tissue structure and imposed electrical current flow in cervical neoplasis; The Lancet; Mar. 11, 2000; vol. 355, Issue 9207: pp. 892-895.
Ellis et al.; Human hydrometry: comparison of multifrequency biolectrical impedance with 2H2O and bromine dilution; Journal of Applied Physiology; 1998; 85(3): 1056-1062.
Jones et al.; Extracellular fluid volume determined by bioelectric impedance and serum albumin in CAPD patients; Nephrology Dialysis Transplantation; 1998; 13: 393-397.
Thomas B.J.; Future technologies; Asia Pacific Journal Clinical Nutrition; 1995; 4: 157-159.
Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; Oct. 31, 1996; 5: 1934-1935.
Woodrow et al.; Effects of icodextrin in automated peritoneal dialysis on blood pressure and bioelectrical impedance analysis; Nephrology Dialysis Transplantation; 2000; 15: 862-866.
Boulier et al.; Fat-Free Mass Estimation by Two Electrode Impedance Method; American Journal of Clinical Nutrition; 1990; 52: 581-585.
McDougal et al.; Body Composition Measurements from Whole Body Resistance and Reactance; Surgical Forum; 1986; 36: 43-44.
Tedner, B.; Equipment using Impedance Technique for Automatic Recording of Fluid-Volume Changes during Hemodialysis; Medical & Biological Engineering & Computing; 1983; 285-290.
Lukaski et al.; Estimation of Body Fluid Volumes using Tetrapolar Bioelectrical Impedance Measurements; Aviation, Space, and Environmental Medicine; Dec. 1988; 1163-1169.
Lozano et al.; Two-frequency impedance plethysmograph: real and imaginary parts; Medical & Biological Engineering & Computing; Jan. 1990; 28(1): 38-42.
Chaudary et al.; Dielectric Properties of Normal & Malignant Human Breast Tissues at Radiowave and Microwave Frequencies; Indian Journal of Biochemistry & Biophysics; 1984; 21(1): 76-79.
Jossinet et al.; A study for breast imaging with a circular array of impedance electrodes; Proc. Vth Int. Conf. Bioelectrical Impedance, 1981, Tokyo, Japan; 1981; 83-86.
Jossinet et al.; Technical Implementation and Evaluation of a Bioelectrical Breast Scanner; Proc. 10.supth Int. Conf. IEEE Engng. Med. Biol., 1988, New Orleans, USA (Imped. Imaging II); 1988; 1: 289.
Man et al.; Results of Preclinical Tests for Breast Cancer Detection by Dielectric Measurements; XII Int. Conf. Med. Biol. Engng. 1979, Jerusalem, Israel. Springer Int., Berlin; 1980; Section 30.4.
Pethig et al.; The Passive Electrical Properties of Biological Systems: Their Significance in Physiology, Biophysics and Biotechnology; Physics in Medicine and Biology; 1987; 32: 933-970.
Piperno et al.; Breast Cancer Screening by Impedance Measurements; Frontiers of Medical & Biological Engineering; 1990; 2: 111-117.
Skidmore et al.; A Data Collection System for Gathering Electrical Impedance Measurements from the Human Breast; Clinical Physics Physiological Measurement; 1987; 8: 99-102.
Sollish et al.; Microprocessor-assisted Screening Techniques; Israel Journal of Medical Sciences; 1981; 17: 859-864.
Surowiec et al.; Dielectric Properties of Breast Carcinima and the Surrounding Tissues; IEEE Transactions on Biomedical Engineering; 1988; 35: 257-263.
Al-Hatib, F.; Patient Instrument Connection Errors in Bioelectrical Impedance Measurement; Physiological Measurement; May 2, 1998; 19(2): 285-296.
Gersing, E.; Impedance Spectroscopy on Living Tissue for Determination of the State of Organs; Bioelectrochemistry and Bioenergetics; 1998; 45: 145-149.
Mattar, J.A.; Application of Total Body Impedance to the Critically Ill Patient; New Horizons; 1996; 4(4): 493-503.
Ott et al.; Bioelectrical Impedance Analysis as a Predictor of Survival in Patients with Human Immunodeficiency Virus Infection; Journal of Acquired Immune Deficiency Syndromes and Human Retrovirology; 1995; 9: 20-25.
Thomas et al.; Bioelectrical impedance analysis for measurement of body fluid volumes—A review; Journal of Clinical Engineering; 1992; 17(16): 505-510.
Ward et al.; There is a better way to measure Lymphedema; National Lymphedema Network Newsletter; Oct. 1995; 7 (4): 89-92.
Cornish et al.; Alteration of the extracellular and total body water volumes measured by multiple frequency bioelectrical impedance analysis; Nutrition Research; 1994; 14(5): 717-727.
Cornish et al.; Early diagnosis of lymphedema using multiple frequency bioimpedance; Lymphology; Mar. 2001; 34: 2-11.
Cornish et al.; Early diagnosis of lymphoedema in postsurgery breast cancer patients; Annals New York Academy of Sciences; May 2000; 571-575.
Brown et al.; Relation between tissue structure and imposed electrical current flow in cervical neoplasia; The Lancet; Mar. 11, 2000; 355 (9207): 892-895.
Iacobellis, G. et al.; Influence of excess fat on cardiac morphology and function: Study in Uncomplicated obesity; Obesity Research; Aug. 8, 2002; 10 (8): 767-773.
Bella, J. N. et al.; Relations of left ventricular mass to fat-free and adipose body mass: The Strong Heart Study; Circulation; Dec. 12, 1998; 98: 2538-2544.
Yoshinaga, M. et al.; Effect of total adipose weight and systemic hypertension on left ventricular mass in children; American Journal of Cardiology; Oct. 15, 1995; 76: 785-787.
Karason, K. et al.; Impact of blood pressure and insulin on the relationship between body fat and left ventricular structure; European Heart Journal; Jan. 1, 2003; 24: 1500-1505.
Abdullah M. Z.; Simulation of an inverse problem in electrical impedance tomography using resistance electrical network analogues; International Journal of Electrical Engineering Education; Oct. 1999; 36 (4): 311-324.
Dines et al.; Analysis of electrical conductivity imaging; Geophysics; Jul. 1981; 46 (7): 1025-1036.
Osterman et al.; Multifrequency electrical impedance imaging: preliminary in vivo experience in breast; Physiological Measurement; Feb. 2000; 21 (1): 99-109.
Ward et al.; Determination of Cole parameters in multiple frequency bioelectrical impedance analysis using only the measurement of impedances; Four-frequency fitting; Physiological Measurement; Sep. 2006; 27 (9): 839-850.
Bernstein; A new stroke volume equation for thoracic electrical bio impedance; Critical Care Medicine; 1986; vol. 14; pp. 904-909.
McAdams et al.; Tissue Impedance: a historical overview; Physiological Measurement, Institute of Physics Publishing, Bristol, GB; 16 (3A); pp. A1-A13; Aug. 1, 1995.
D'Entremont et al. "Impedance spectroscopy: an accurate method of differentiating between viable and ischaemic or infarcted muscle tissue" Med. Biol. Eng. Comput., 2002, 40: 380-87.
Zhu et al., "Dynamics of segmental extracellular volumes during changes in body position by bioimpedance analysis"; J. App. Physiol.; 1998, vol. 85, pp. 497-504.
McCullagh, W. A., et al., Bioelectrical impedance analysis measures the ejection fraction of the calf muscle pump, IFMBE Proceedings, 2007; vol. 17, p. 619.
U.S. Appl. No. 13/128,631, Essex et al.

(56) References Cited

OTHER PUBLICATIONS

U.S. Appl. No. 13/131,859, Gaw.
U.S. Appl. No. 12/090,078, filed Feb. 12, 2009, Chetham.
English Translation of CN1180513A published May 6, 1998.
English Translation of CN12336597 published Dec. 1, 1999.
English Translation of CN1329875A published Jan. 9, 2002.
English Translation of JP2001037735 published Feb. 13, 2001.
English Translation of JP2001061804 published Mar. 13, 2001.
English Translation of JP2002502274 published Jan. 22, 2002.
English Translation of JP2003502092 published Jan. 21, 2003.
English Translation of JP2006501892 published Jan. 19, 2006.
English Translation of JP2008502382 published Jan. 31, 2008.
English Translation of JP2010526604 published Aug. 5, 2010.
English Abstract for WO9948422 published Sep. 30, 1999.
English Abstract for WO0152733 published Jul. 26, 2001.
Bernstein, "A new stroke volume equation for thoracic electrical bioimpedance: Theory and rationale," Critical Care Medicine,1986, pp. 904-909, vol. 14, No. 10.
Blad and Baldetorp, "Impedance spectra of tumour tissue in comparison with normal tissue; a possible clinical application for electrical impedance tomography," Physiol. Meas., 1996, pp. A105-A115, vol. 17.
Lorenzo et al., "Determination of Intracelllar Water by Multifrequency Bioelectrical Impedance," Ann. Nutr. Metab., 1995, pp. 177-184, vol. 39.
Edwards, "A Modified Pseudosection for Resistivity and IP," Geophysics, Aug. 1977, pp. 1020-1036, vol. 42, No. 5.
Hansen, "On the influence of shape and variations in conductivity of the sample on four-point measurements," Appl. Sci. Res., 1959, pp. 93-104, Section B, vol. 8.
Igel, "On the Small-Scale Variability of Electrical Soil Properties and its Influence on Geophysical Measurements," Dissertation, University of Frankfurt, 2007, pp. 1-188.
Kyle et al., "Bioelectrical impedance analysis—part I: review of principals and methods," Clinical Nutrition, 2004, pp. 1226-1243, vol. 23.
Loke and Barker, "Least-squares deconvolution of apparent resistivity pseudosections," Geophysics, Nov.-Dec. 1995, pp. 1682-1690, vol. 60, No. 6.
McAdams and Jossinet, "Tissue impedance: a historical overview," Physiol. Meas., 1995, pp. A1-A13, vol. 16.
McEwan and Holder, "Battery powered and wireless Electrical Impedance Tomography Spectroscopy Imaging using Bluetooth," IFMBE Proceedings, 2007, pp. 798-801, vol. 16.
Roy and Apparao, "Depth of investigation in direct current methods," Geophysics, Oct. 1971, pp. 943-959, vol. 36, No. 5.
Wilson et al., "Feasibility studies of electrical impedance spectroscopy for monitoring tissue response to photodynamic therapy," SPIE, May 1998, pp. 69-80, vol. 3247.
Scharfetter, Effect of postural changes on the reliability of volume estimations from bioimpedance spectroscopy data, Kidney International Apr 1997, vol. 51, No. 4, pp. 1078-1087.
Ezenwa, Multiple frequency system for body composition measurement, Medical Informatics, Ethics, Cardiology, Instrumentation., Proceedings of the Annual International Conference of the Engineering in Medicine and Biology Society, Oct. 28, 1993, vol. 15, Part 02.
Yamakoshi, Non-Invasive Cardiovascular Hemodynamic Measurements, Sensors in Medicine and Health Care, 2004, pp. 107-160.
Ivorra, Bioimpedance dispersion width as a parameter to monitor living tissues, Physiological Measurement, 2005, vol. 26, S165-S173.
Golden, J, et al., Assessment of peripheral hemodynamics using impedance plethysmogrphy, Physical Therapy, 1986, vol. 66, No. 10, pp. 1544-1547.
Kim, Y et al., Impedance tomography and its application in deep venous thrombosis detection, IEEE Engineering in Medicine and Biology Magazine, IEEE Service Center, Pisacataway, NJ, US, Mar. 1, 1989, vol. 8, No. 1, pp. 46-49.
Fenech, M, et al., Extracellular and intracellular volume variations during postural change measured by segmental and wrist-ankle bioimpedance spectroscopy, IEEE transactions on biomedical engineering, IEEE Service Center, Piscataway, NJ, US, Jan. 1, 2004, vol. 51, No. 1, pp. 166-175.
Stanton, AWB, et al., Non-invasive assessment of the lymphedematous limb, Lymphology, The International Society of Lymphology, 2000, vol. 33, No. 3 pp. 122-135.
Cornish, Bruce H, et al., A new technique for the quantification of peripheral edema with application in both unilateral and bilateral cases, Angiology, 2002, vol. 53, No. 1, pp. 41-47.
Seo, A, et al., Measuring lower leg swelling: Optiumum frequency for impedance method, Medical & Biological Engineering & Computing, Mar. 1, 2001, vol. 39, pp. 185-189.
Smith, JG, et al., A pilot study for tissue characterization using bio-impedance mapping, 13th International Conference on Electrical Bio-impedance and the 8th Conference on Electrical Impedance Tomography 2007, pp. 146-149.
Nawarycz, T, et al., Triple-frequency electroimpedance method for evaluation of body water compartments, Medical & Biological Engineering & Computing, Jan. 1, 1996, vol. 34, No. Supp. 01, Pt 02, pp. 181-182.
Noshiro, M, et al., Electrical impedance in the lower limbs of patients with duchenne muscular dystrophy: A preliminary study, Medical & Biological Engineering & Computing, Mar. 1, 1993, vol. 31, No. 2, pp. 97-102.
Seoane, F, et al., Current source for wideband electrical bioimpedance spectroscopy based on a single operational amplifier, World Congress on Medical Physics and Biomedical Engineering 2006, Jan. 1, 2007, vol. 14 pp. 707-710.
Cornish, BH, et al., Optimizing electrode sites for segmental bioimpedance measurements, Physiological Measurement, Institute of Physics, Aug. 1, 1999, vol. 20, No. 3, pp. 241-250.

* cited by examiner

MONITORING SYSTEM AND PROBE

BACKGROUND OF THE INVENTION

The present invention relates to a method and apparatus for use in analysing impedance measurements performed on a subject, and in particular to a probe that can be used in determining a limb impedance profile, which can in turn be used in determining the presence, absence or degree of oedema in a subject's limb.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Lymphoedema is a condition characterised by excess protein and oedema in the tissues as a result of reduced lymphatic transport capacity and/or reduced tissue proteolytic capacity in the presence of a normal lymphatic load. Acquired, or secondary lymphoedema, is caused by damaged or blocked lymphatic vessels. The commonest inciting events are surgery and/or radiotherapy.

For example, upper limb lymphoedema is a common sequela of treatment for breast cancer. Estimates of the incidence of breast cancer lymphoedema vary in the medical literature from low values in the range of 9%-10% to those that exceed 50%. Lymphoedema is associated with a reduced quality of life, particularly emotional, social and physical function, as well as body image and lifestyle.

The condition is incurable and has been found difficult to treat with drugs or surgery but symptomatic treatment by complex physical therapy has been shown to benefit patients. Critical to patient management is that the extent of lymphoedema be measured regularly to assess patient's progress. A decrease in limb size not only indicates that treatment is beneficial but also helps encourage patient compliance with a demanding treatment programme. Additionally, onset of lymphoedema is unpredictable and may develop within days of its cause or at any time during a period of many years after that cause.

Accordingly, there is a need to be able to easily monitor for and diagnose the presence or degree of lymphoedema. A variety of methods have been used ranging in complexity from sophisticated imaging techniques such as MRI to simple geometrical volume calculations from limb circumference measurements. However, these techniques are either too costly, in the case of MRI, or insufficiently accurate in the case of limb circumference.

One existing technique for determining biological parameters relating to a subject, such as fluid levels, involves the use of bioelectrical impedance. This involves measuring the electrical impedance of a subject's body using a series of electrodes placed on the skin surface. Changes in electrical impedance at the body's surface are used to determine parameters, such as changes in fluid levels, associated with the cardiac cycle or oedema.

WO00/79255 describes a method of detection of oedema, such as lymphoedema by measuring bioelectrical impedance at two different anatomical regions in the same subject at a single low frequency alternating current. The two measurements are analysed to obtain an indication of the presence of tissue oedema by comparing with data obtained from a normal population.

However, whilst such techniques can be used to determine the presence of oedema over an entire limb, lymphoedema can be highly localised, and as the resolution of such techniques can be limited, this makes the detection of such localised oedema difficult.

SUMMARY OF THE PRESENT INVENTION

In a first broad form the present invention provides a probe method for use in performing impedance measurements on a subject, the probe including:
 a) a housing configured to be held by an operator in use;
 b) a contact surface for contacting the subject; and,
 c) a connector for connecting the contact surface to a measuring device.

Typically the housing is an elongate housing, the contact surface is provided at a first end of the housing and the connector is provided at a second opposing end of the housing.

Typically the housing is formed from an insulating material.

Typically the housing is formed from a perspex tube.

Typically the contact surface has a convex shape.

Typically the contact surface includes a moving member for moving relative to the subject.

Typically the moving member is a roller ball, and wherein the housing includes a shaped mounting for receiving the roller ball.

Typically the moving member is a cylindrical roller mounted on an axle.

Typically the probe includes a contact for electrically connecting the moving member to the connecter.

Typically the contact is a spring.

Typically the probe includes a sensor for sensing movement of the moving member.

Typically the sensor includes at least one of:
 a) an optical sensor; and,
 b) moving elements in contact with the moving member.

Typically the connector is for connecting to a lead of a measuring device.

Typically, in use, the probe is moved along a segment of the subject to thereby allow an impedance profile representing variations in impedance along the segment to be determined.

Typically, in use, the probe is connected to a measuring device the measuring device including, a processing system for:
 a) causing at least one electrical signal to be applied to the subject via first electrodes provided on the subject; and,
 b) determining an indication indicative of at least one second electrical signal measured via a second electrode positioned on the subject, and via the probe.

In a second broad form the present invention provides a method of performing impedance measurements on a subject using a probe, the probe including a housing configured to be held by an operator in use, a contact surface for contacting the subject and a connector for connecting the contact surface to a measuring device, the method including:
 a) positioning the probe in contact with a segment of the subject;
 b) causing the measuring device to perform a sequence of impedance measurements; and, c) moving the probe along the segment during the sequence of impedance measurements so that the measuring device determines impedance measurements along the segment.

Typically the method includes, in the measuring device:
a) using the impedance measurements to determine an impedance profile; and,
b) displaying a representation of the impedance profile to thereby allow the impedance profile to be used in determining a presence, absence, degree or location of oedema in the subject.

Typically the method includes, in the measuring device:
a) causing a sequence of first electrical signals to be applied to the subject via first electrodes provided on the subject; and,
b) determining an indication of a sequence of second electrical signals measured via a second electrode positioned on the subject, and via the probe.

Typically the method includes, in the measuring device: using an indication of the first and second signals to determine an impedance profile, the impedance profile representing variations in measured impedance along the segment.

In a third broad form the present invention provides a method for use in analysing impedance measurements performed on a subject, the method including, in a processing system:
a) determining a sequence of impedance values measured along a segment of the subject; and,
b) determining an impedance profile using the sequence of impedance values.

Typically the method includes, in the processing system, displaying a representation of the impedance profile to thereby allow the impedance profile to be used in determining a presence, absence, degree or location of oedema in the subject.

Typically the method includes in the processing system:
a) causing a sequence of first signals to be applied to the subject via first electrodes provided on the subject;
b) determining an indication indicative of a sequence of second electrical signals measured via second electrodes provided on the subject; and,
c) determining the sequence of impedance values using indications of the sequences of first and second signals.

Typically one of the second electrodes is a probe, and wherein the method includes determining an indication of at least some of the second electrical signals as the probe is moved along the segment.

Typically the method includes:
a) positioning the probe in contact with a segment of the subject;
b) causing the processing system to perform a sequence of impedance measurements; and,
c) moving the probe along the segment during the sequence of impedance measurements so that the measuring device determines impedance measurements along the segment.

Typically the method includes, in the processing system:
a) determining one or more impedance parameter values from measured impedance values; and,
b) determining the impedance profile using the impedance parameter values.

Typically the impedance parameter values include at least one of:
a) an impedance at infinite applied frequency ($R_\infty$);
b) an impedance at zero applied frequency ($R_0$); and,
c) an impedance at a characteristic frequency ($Z_c$).

Typically the method includes, in the processing system, determining the impedance parameter values at least in part using the equation:

$$Z = R_\infty + \frac{R_0 - R_\infty}{1 + (j\omega\tau)^{(1-\alpha)}}$$

where: $R_\infty$=impedance at infinite applied frequency;
$R_0$=impedance at zero applied frequency;
$\omega$=angular frequency;
$\tau$ is the time constant of a capacitive circuit modelling the subject response; and,
$\alpha$ has a value between 0 and 1.

Typically the representation includes at least one of:
a) a baseline impedance profile for the segment;
b) a reference impedance profile derived from a normal population; and,
c) an impedance profile for a contra-lateral segment.

Typically the method includes, in the processing system:
a) determining one or more subject details; and,
b) selecting a reference at least partially in accordance with the subject details.

Typically the subject details include at least one of:
a) limb dominance;
b) ethnicity;
c) age;
d) sex;
e) weight; and,
f) height.

Typically one of the second electrodes is formed from a band electrode including:
a) a substrate having provided thereon:
  i) a number of electrically conductive contact pads; and,
  ii) a corresponding number of electrically conductive tracks, each track extending from an edge of the substrate to a respective contact pad;
b) an insulating layer provided on the substrate, the insulating layer including a number of apertures, and being positioned to thereby overlay the tracks with at least a portion of each pad contact aligned with a respective aperture; and,
c) an electrically conductive medium provided in the apertures.

Typically the method includes measuring the sequence of second electrical signals via the contact pads.

In a fourth broad form the present invention provides apparatus for use in analysing impedance measurements performed on a subject, the apparatus including a processing system for:
a) determining a sequence of impedance values measured along a segment of the subject; and,
b) determining an impedance profile using the sequence of impedance values.

Typically the apparatus includes:
a) a signal generator for applying one or more electrical signals to the subject using a first set of electrodes;
b) a sensor for measuring electrical signals measured across a second set of electrodes; and,
c) a controller for:
  i) controlling the signal generator; and,
  ii) determining the indication of the measured electrical signals.

Typically at least one of the second electrodes is a probe, the probe including:

a) a housing configured to be held by an operator in use;
b) a contact surface for contacting the subject; and,
c) a connector for connecting the contact surface to the sensor.

In a fifth broad form the present invention provides a probe for use in diagnosing oedema in a body segment of a subject, the probe including:
a) a housing configured to be held by an operator in use;
b) a contact surface for contacting the segment of the subject; and,
c) a connector for connecting the contact surface to a measuring device.

In a sixth broad form the present invention provides a method of diagnosing oedema in a body segment of a subject using a probe, the probe including a housing configured to be held by an operator in use, a contact surface for contacting the subject and a connector for connecting the contact surface to a measuring device, the method including:
a) positioning the probe in contact with a segment of the subject;
b) causing the measuring device to perform a sequence of impedance measurements;
c) moving the probe along the segment during the sequence of impedance measurements so that the measuring device determines impedance measurements along the segment; and,
d) determining an impedance profile using the sequence of impedance values, the impedance profile being indicative of a presence, absence, degree or location of oedema in the subject.

In a seventh broad form the present invention provides a method for use in diagnosing oedema in a body segment of a subject, the method including, in a processing system:
a) determining a sequence of impedance values measured along a segment of the subject; and,
b) determining an impedance profile using the sequence of impedance values, the impedance profile being indicative of a presence, absence, degree or location of oedema in the subject.

In an eighth broad form the present invention provides apparatus for use in diagnosing oedema in a body segment of a subject, the apparatus including a processing system for:
a) determining a sequence of impedance values measured along a segment of the subject; and,
b) determining an impedance profile using the sequence of impedance values, the impedance profile being indicative of a presence, absence, degree or location of oedema in the subject.

It will be appreciated that the broad forms of the invention may be used individually or in combination, and may be used for diagnosis of the presence, absence or degree of a range of conditions and illnesses, including, but not limited to oedema, lymphoedema, body composition and the like.

BRIEF DESCRIPTION OF THE DRAWINGS

An example of the present invention will now be described with reference to the accompanying drawings, in which: —

DETAILED DESCRIPTION OF THE PREFERRED EMBODIMENTS

Figure 1:
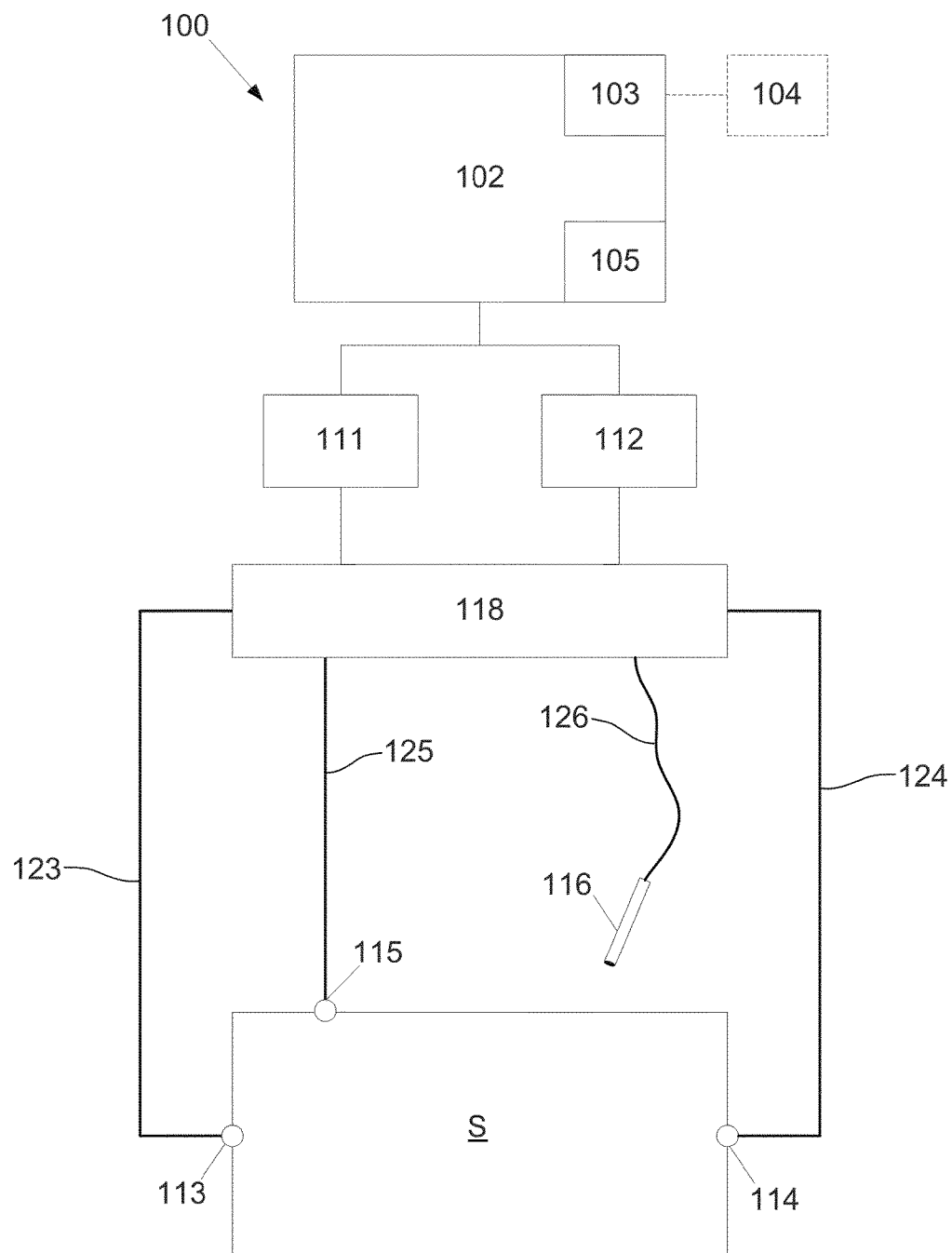
FIG. 1 is a schematic diagram of an example of impedance determination apparatus.

An example of apparatus suitable for performing an analysis of a subject's bioelectric impedance will now be described with reference to FIG. 1.

As shown the apparatus includes a measuring device 100 including a processing system 102 coupled to a signal generator 111 and a sensor 112. In use the signal generator 111 and the sensor 112 are coupled to first electrodes 113, 114, and second electrodes 115, 116, provided on a subject S, via respective first leads 123, 124, and second leads 125, 126. In this example, the second electrode 116 is in the form of a probe electrode 116 that can be moved over the subject S, during the impedance measurement procedure, as will be described in more detail below.

The connection may be via a switching device 118, such as a multiplexer, allowing the leads 123, 124, 125, 126 to be selectively interconnected to signal generator 111 and the sensor 112, although this is not essential, and connections may be made directly between the signal generator 111 and the first electrodes 113, 114, and the sensor 112 and the second electrodes 115, 116.

An optional external interface 103 can be used to couple the measuring device 100, via wired, wireless or network connections, to one or more peripheral devices 104, such as an external database or computer system, barcode scanner, or the like. The processing system 102 will also typically include an I/O device 105, which may be of any suitable form such as a touch screen, a keypad and display, or the like.

In use, the processing system 102 is adapted to generate control signals, which causes the signal generator 111 to generate one or more alternating signals, such as voltage or current signals, which can be applied to a subject S, via the first electrodes 113, 114. The sensor 112 then determines the voltage across or current through the subject S, using the second electrodes 115, 116 and transfers appropriate signals to the processing system 102.

Accordingly, it will be appreciated that the processing system 102 may be any form of processing system which is suitable for generating appropriate control signals and interpreting an indication of the measured signals to thereby determine the subject's bioelectrical impedance, and optionally determine other information such as the presence, absence or degree of oedema, or the like.

The processing system 102 may therefore be a suitably programmed computer system, such as a laptop, desktop, PDA, smart phone or the like. Alternatively the processing system 102 may be formed from specialised hardware, such as an FPGA (field programmable gate array), or a combination of a programmed computer system and specialised hardware, or the like.

It will be appreciated that the processing system 102, the signal generator 111 and the sensor 112 may be integrated into a common housing and therefore form an integrated device. Alternatively, the processing system 102 may be connected to the signal generator 111 and the sensor 112 via wired or wireless connections. This allows the processing system 102 to be provided remotely to the signal generator 111 and the sensor 112. Thus, the signal generator 111 and the sensor 112 may be provided in a unit near, or worn by the subject S, whilst the processing system 102 is situated remotely to the subject S.

In use, the first electrodes 113, 114 are positioned on the subject to act as drive electrodes allowing one or more signals to be injected into the subject S. The location of the first electrodes 113, 114 will depend on the segment of the subject S under study, and can include for example, positioning electrodes on the wrist and ankles of a subject, to allow the impedance of limbs to be determined.

Once the second electrodes 115, 116 are also positioned as will be described below, one or more alternating signals are applied to the subject S, via the first leads 123, 124 and the first electrodes 113, 114. The nature of the alternating signal will vary depending on the nature of the measuring device and the subsequent analysis being performed.

For example, the system can use Bioimpedance Analysis (BIA) in which a single low frequency current is injected into the subject S, with the measured impedance being used directly in the assessment of oedema. In contrast Bioimpedance Spectroscopy (BIS) devices utilise frequencies ranging from very low frequencies (4 kHz) to higher frequencies (1000 kHz), and can use 256 or more different frequencies within this range, to allow multiple impedance measurements to be made within this range.

Thus, the measuring device 100 may either apply an alternating signal at a single frequency, at a plurality of frequencies simultaneously, or by apply a number of alternating signals at different frequencies sequentially, depending on the preferred implementation. The frequency or frequency range of the applied signals may also depend on the analysis being performed.

In one example, the applied signal is a frequency rich current from a current source clamped, or otherwise limited, so it does not exceed a maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between the second electrodes 115, 116. The acquired signal and the measured signal will be a superposition of potentials generated by the human body, such as the ECG, and potentials generated by the applied current.

Optionally the distance between the second electrodes may be measured and recorded. Similarly, other parameters relating to the subject may be recorded, such as the height, weight, age, sex, health status, any interventions and the date and time on which they occurred. Other information, such as current medication, may also be recorded.

To assist accurate measurement of the impedance, buffer circuits may be placed in connectors that are used to connect the second electrodes 115, 116 to the second leads 125, 126, as will be described in more detail below. This ensures accurate sensing of the voltage response of the subject S, and in particular helps eliminate contributions to the measured voltage due to the response of the second leads 125, 126, and reduce signal loss.

This in turn greatly reduces artefacts caused by movement of the second leads 125, 126, which is particularly important in some applications such as monitoring fluid levels during dialysis, in which sessions usually last for several hours and the subject will move around and change positions during this time, as well as being important during movement of the probe 116.

A further option is for the voltage to be measured differentially, meaning that the sensor used to measure the potential at each second electrode 115, 116 only needs to measure half of the potential as compared to a single ended system.

The measurement system may also have buffers placed in the connectors between the first electrodes 113, 114 and the first leads 123, 124. In one example, current can also be driven or sourced through the subject S differentially, which again greatly reduced the parasitic capacitances by halving the common-mode current. Another particular advantage of using a differential system is that the micro-electronics built into the connectors for each first electrode 113, 114 also removes parasitic capacitances that arise when the subject S, and hence the leads first 123, 124, move.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

In the case of BIS, impedance or admittance measurements are determined from the signals at each frequency by comparing the recorded voltage and current signal. The demodulation algorithm will produce an amplitude and phase signal at each frequency.

Figure 2:
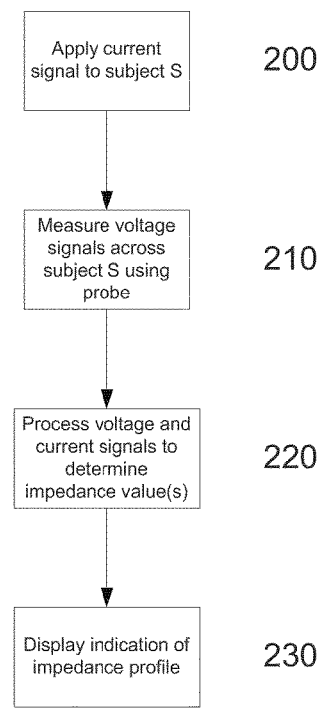
FIG. 2 is a flowchart of an example of a process for determining an impedance profile.

An example of the operation of the apparatus to generate an impedance profile will now be described with reference to FIG. 2.

In this example, at step 200 the processing system 102 causes a current signal to be applied to the subject S, with the induced voltage across the subject S being measured at step 210, with signals representing the measured voltage and the applied current being returned to the processing system 102 for analysis.

This is typically performed for at least a segment of the subject S that is suspected of being susceptible to oedema, and may also be repeated for a separate healthy segment of the subject. Thus, for example, in the case of limb oedema, this is typically performed on the affected or "at risk" limb (hereinafter generally referred to as the "affected" limb), and may also be performed on the contra-lateral limb.

During this process, the probe electrode 116 will be moved along the length of the respective limb or limb segment, so that a number of measurements are taken over the entire limb or segment length. In one example, the measurements for a single limb or segment are taken over a time period such as 20 seconds, with measurements being made at a sampling rate of 1 ms, thereby providing a total of 20,000 readings for the limb, with the readings being distributed along the limb length. However, any suitable number of readings may be used, although it will be appreciated that the greater the number of measurements made, the higher the resolution of the impedance profile.

It will be appreciated that the application of the current and voltage signals may be controlled by a separate processing system to that used in performing the analysis to derive an impedance profile, and that the use of a single processing system is for the purpose of example only.

At step 220, measured voltage and current signals are used by the processing system 102 to determine a sequence of measured impedance values. In one example, this includes first impedance values representing the impedance profile of the unaffected limb or limb segment and second impedance values representing the impedance profile of the affected limb or limb segment, although this is not essential, and in one example, impedance measurements are only made for the affected limb or limb segment.

Once the impedance values are determined, these are used by the processing system 102, to derive an impedance profile. This may be achieved in any one of a number of ways depending on the preferred implementation.

In one example, the impedance profile is in the form of a graphical representation showing the variation in the measured impedance values along the length of the limb or limb segment. It will be appreciated that in one example, this involves measuring the position of the probe along the limb or limb segment, allowing the impedance value to be plotted against position. However, a number of variations on this are possible.

For example, it can be assumed that movement of the probe along the limb is performed at a relatively constant rate, in which case subsequently sampled measurements will be evenly spaced with respect to each other, on the resulting profile. Alternatively, the position can be derived from the impedance values themselves, as some portions of limbs, such as elbow or knee joints, have different impedance values to other portions of the limb, allowing the elbow or knee to be easily identified.

Additionally, or alternatively, the impedance profile can be based on parameters derived from measured impedance values, such as the impedance at zero, characteristic or infinite frequencies ($R_0$, $Z_c$, $R_\infty$).

The impedance profile can be based solely on the impedance measured for the "affected" limb or limb segment. However, alternatively, the impedance profile can also include an indication of the impedances measured for the unaffected limb or limb segment, thereby allowing comparison between the limbs or segments. It will be appreciated that in a healthy person, the impedance of both limbs or corresponding limb segments will be similar, and consequently, differences in the impedance profiles can be used to help identify the presence, absence, degree and/or location of any oedema.

Additionally, and/or alternatively, the impedance profile can include a baseline or other reference. The baseline is typically a previous impedance profile measured for the same limb, or limb segment of the subject S, whereas the reference is typically determined from a reference population of healthy individuals, as will be described in more detail below.

Once the impedance profile is determined, a representation of the impedance profile can be displayed to an operator at step 230, as will be described in more detail below.

Figure 3A:
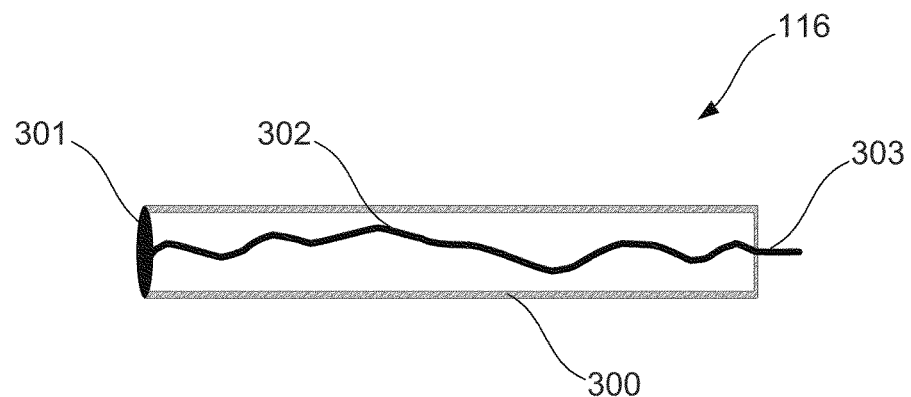
FIGS. 3A to 3C are schematic diagrams of examples of impedance measuring probes.

A first example of a probe electrode for use in determining an impedance profile will now be described with reference to FIG. 3A.

In this example, the probe electrode 116 is formed from a housing 300 and a contact surface 301. The contact surface 301 is connected via an electrical connection 302 to a connector 303 which allows onward connection to the lead 126 shown in FIG. 1.

In use the contact surface 301 is designed to be placed against the subject S, in contact with the subject's skin surface. To ensure accurate measurements are obtained, it is important to ensure good electrical contact between the contact surface 301 and the subject S, and accordingly, the contact surface 301 is typically formed from an electrically conductive material, such as stainless steel or the like, and may also be coated with an electro-conductive gel. In this example, the contact surface 301 is formed from a convex curved smooth surface, to assist with smooth transit across the subject's skin, as the probe 116 is moved along the length of the subject's limb, as well as to maximise contact between the contact surface and the subject's skin, thereby ensuring good electrical connection.

The housing is configured to allow an operator to hold the probe electrode whilst it is placed in contact with the subject. To ensure that this does not interfere with measurements, the housing is typically formed from an electrically insulating material such as a Perspex tube, or the like, although a wide variety of probe arrangements may be used.

Figure 3B:
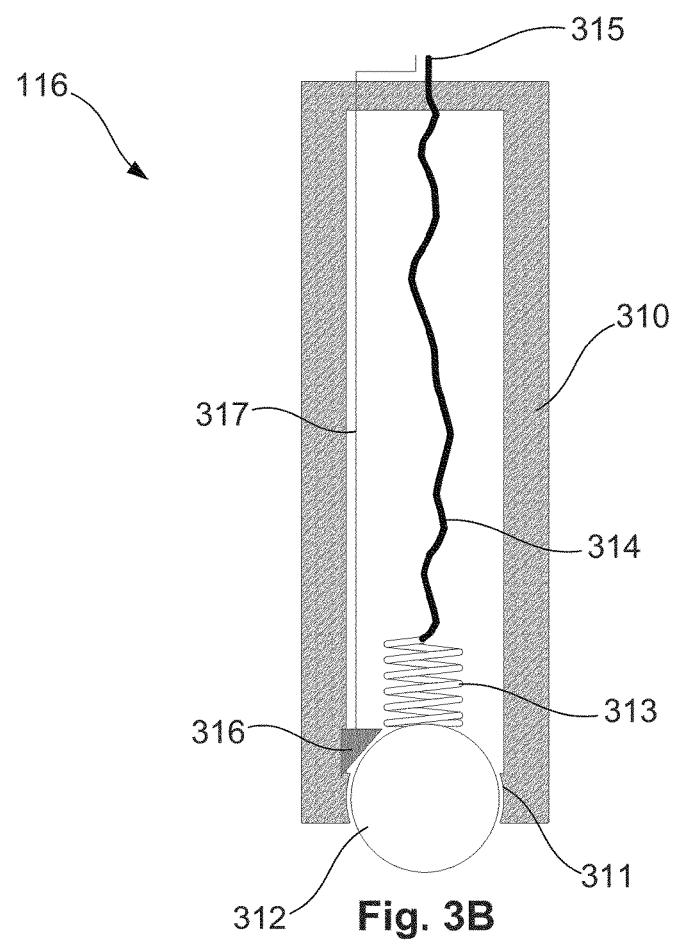
Figure 3C:
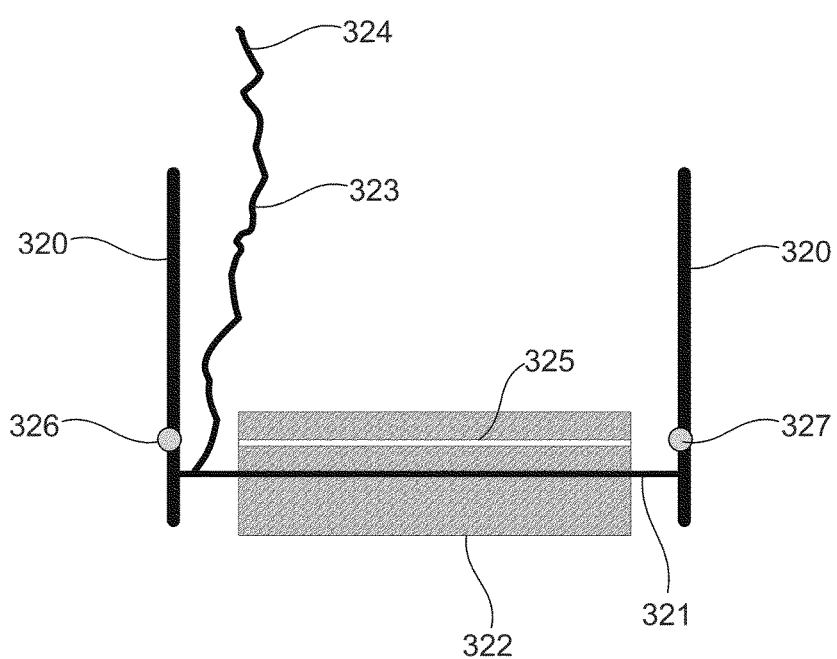

Alternative probe arrangements are shown in FIGS. 3B and 3C.

In the example of FIG. 3B the contact surface 301 is provided by a moving member, such as a roller ball arrangement. Accordingly in this instance the probe 116 is formed from a housing 310, such as a Perspex tube or the like. The housing 310 includes a shaped end portion, shown generally at 311, which forms a mounting adapted to receive a roller ball 312. The roller ball 312 is positioned in the shaped portion 311 to allow rotational movement of the roller ball in any direction, whilst constraining translational movement. The roller ball 312 is generally formed from an electrically conducted substance such as stainless steel or the like, and may again be coated with an electrically conductive gel.

A compression spring 313 is mounted in the housing a mounting (not shown), so that the spring is urged into contact with the roller ball 312 thereby ensuring good electrical contact between the roller ball 312 and the spring 313. The spring 313 is then connected via an electrical connection 314 to a connector 315 which in turn allows the probe to be connected to the lead 126. However, any suitable method of electrically connecting the roller ball 312 and the lead 126 may be used, such as brushes, or the like.

In addition to the provision of the roller ball 312, in this example the probe 116 also includes a motion sensing system 316 configured to sense motion of the roller ball 312 and return an indication of the motion via an electrical connection 317. This would typically involve transferring signals indicative of movement of the roller ball 312, via the lead 126, or an appropriate other connection, to the measuring device 100.

It will be appreciated by persons skilled in the art that the mechanism for sensing motion of the roller ball 312 may be any appropriate mechanism. Thus, for example, the sensor 316 can include optical sensors adapted to optically detect movement of the roller ball. Alternatively, one or more moving elements, such as wheels, can be placed in contact with the roller ball 312 such that movement of the moving element can be detected. It will be appreciated that the ability to detect motion of a roller ball 312 is technology known from computer mouse or trackball peripheral devices, or the like, and accordingly this will not be described in any further detail.

A third example probe arrangement is shown at FIG. 3C. In this example the probe 116 includes two supports 320 which operate to support an axle 321. An electrically conductive roller 322, such as a stainless steel roller, is mounted to the axle with the roller 322 being positioned against the subject in use. The axle 321, which is also conductive, is connected via an electrical connection 323 to a connector 324 to allow onward connectivity to the lead 126.

In this example, motion of the roller 322, for example to detect the distance moved by the probe 116 along a limb, can be detected in any one of a number of ways. In this example the roller 322 includes an aperture 325 extending therethrough. The aperture 325 is positioned so that once per revolution of the roller 322 the aperture 325 aligns with a radiation source 326, such as an LED (light emitting diode) and a corresponding detector 327. Accordingly, when the aperture 325 aligns with the radiation source 326 and detector 327, the detector 327 will detect radiation emitted by the source by allowing revolutions of the roller 322 to be counted. Again information regarding this can be transferred back to the measuring device utilising appropriate connections (not shown).

Figure 4:
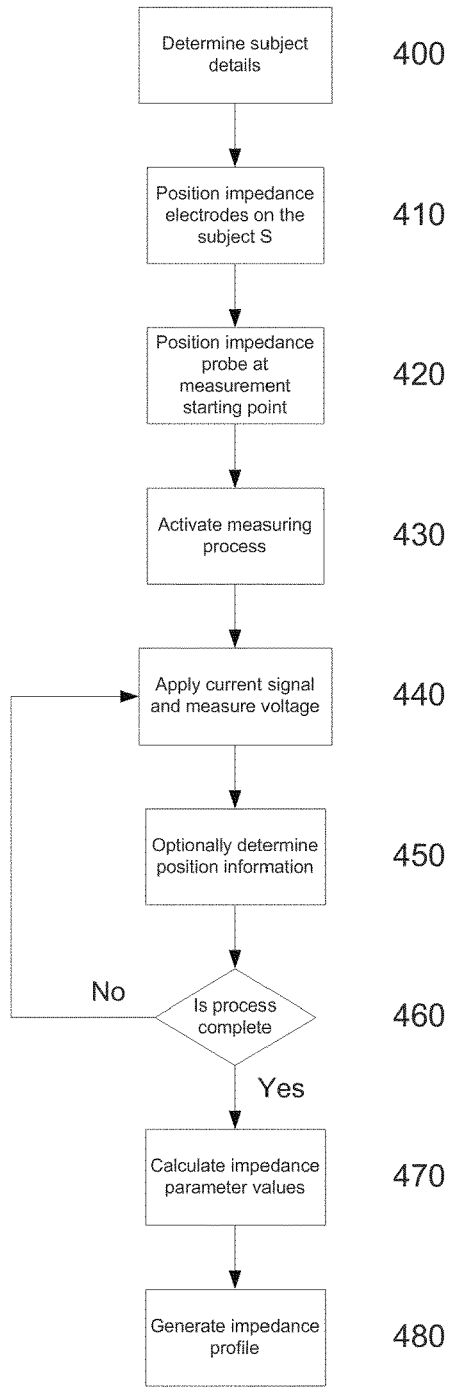
FIG. 4 is a flowchart of an example of a process for determining an impedance profile for uni-lateral limb oedema.

Operation of the probe 116 for use in determining the impedance profile of the subject's limb will now be described with reference to FIG. 4. For the purpose of this example, measurements to determine a profile are performed along the entire length of the limb, but it will be appreciated that this can also be applied to limb segment or other body segments.

In this example, at step 400 subject details are optionally determined and provided to the processing system 102. The subject details will typically include information such as limb dominance, details of any medical interventions, as well as information regarding the subject as the subject's age, weight, height, sex, ethnicity or the like. The subject details can be used in referencing previous measurements made for the subject, for selecting other baselines or reference normal population values, as well as for generating reports, or the like.

It will be appreciated that the subject details may be supplied to the processing system 102 via appropriate input means, such as the I/O device 105. Thus, each time a subject measurement is performed this information can be input into the measuring device 100.

However, more typically the information is input a single time and stored in an appropriate database, or the like, which may be connected as a peripheral device 104 via the external interface 103. The database can include subject data representing the subject details, together with information regarding previous impedance profiles, baseline measurements or impedance measurements recorded for the subject.

In this instance, when the operator is required to provide subject details, the operator can use the processing system 102 to select a search database option allowing the subject details to be retrieved. This is typically performed on the basis of a subject identifier, such as a unique number assigned to the individual upon admission to a medical institution, or may alternatively be performed on the basis of name or the like. Such a database is generally in the form of an HL7 compliant remote database, although any suitable database may be used.

In one example, the subject can be provided with a wristband or other device, which includes coded data indicative of the subject identifier. In this case, the measuring device 100 can be coupled to a peripheral device 104, such as a barcode or RFID (Radio Frequency Identification) reader allowing the subject identifier to be detected and provided to the processing system 102, which in turn allows the subject details to be retrieved from the database. The processing system 102 can then display an indication of the subject details retrieved from the database, allowing the operator to review these and confirm their accuracy before proceeding further.

As part of this process, an affected limb, or "at risk" limb, may be determined. This may be achieved in any one of a number of ways depending on the preferred implementation. Thus, for example, the affected limb can be indicated through the use of appropriate input means, such as the I/O device 105. Alternatively this information can be derived directly from the subject details, which may include an indication of the affected limb, or details of any medical interventions performed, which are in turn indicative of the affected limb.

At step 410 an operator positions the first electrodes 113, 114, and the second electrode 115 on the subject S, and connects these electrodes to the corresponding leads 123, 124, 125. The probe is also connected to the lead 126, if required.

Figure 5A:
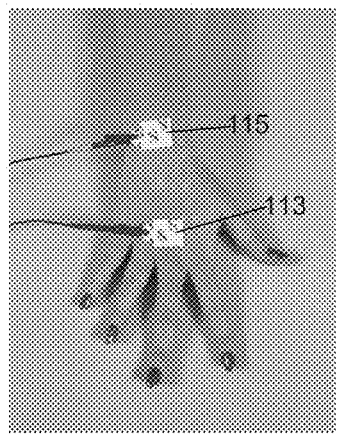
FIGS. 5A and 5B are diagrams of examples of electrode positions for use in measuring limb impedances.
Figure 5B:
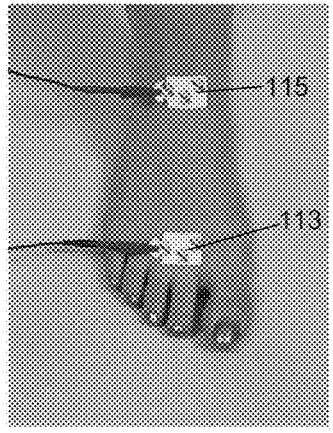
Figure 5C:
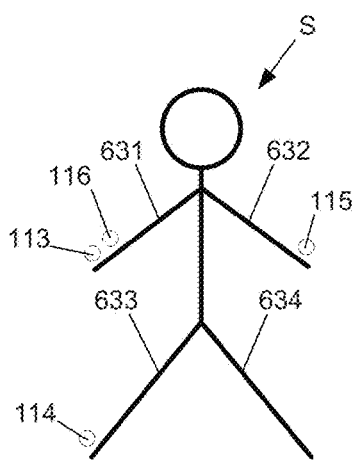
FIGS. 5C and 5D are schematic diagrams of examples of electrode positions for use in measuring limb impedances.
Figure 5D:
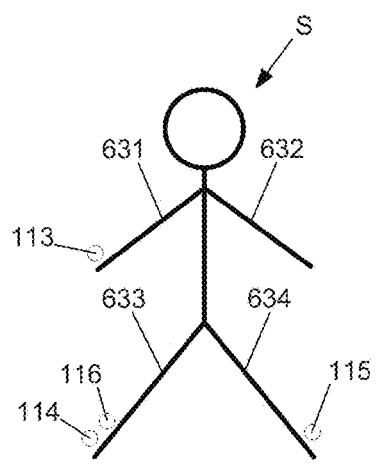

The general arrangement is to provide electrodes on the hand at the base of the knuckles and between the bony protuberances of the wrist, as shown in FIG. 5A, and on the feet at the base of the toes and at the front of the ankle, as shown in FIG. 5B. The configurations shown in FIGS. 5C and 5D allow impedance profiles of the right arm 631 and the right leg 633 to be measured respectively, and it will be appreciated that equivalent arrangements can be used to derive impedance profiles for the left leg and left arm.

As a result of the electrode positioning, as the probe 116 is moved from the wrist towards the shoulder along the right arm 631, the value of the measured impedance will tend to drop, as the theory of equal potentials, indicates that the potential measured at the electrode 115 will be similar to the potential at the shoulder of the right arm 631.

It will be appreciated that using an electrode arrangement in this manner allows the electrode positions to provide reproducible results for impedance measurements. For example when current is injected between electrodes 113 and 114 in FIG. 5C, the electrode 115 could be placed anywhere along the left arm 632, since the whole arm is at an equal potential, equivalent to if the electrode were positioned at the shoulder.

This is advantageous as it greatly reduces the variations in measurements caused by poor placement of the electrodes by the operator. It also greatly reduces the number of electrodes required to perform segmental body measurements, as well as allowing the limited connections shown to be used to measure each of limbs separately.

However, it will be appreciated that any suitable electrode and lead arrangement may be used.

At step 420 the impedance probe is positioned at a start measuring point. The start measuring point may vary depending on the particular measurements being made. Thus for example, in determining an arm limb impedance profile the probe 116 is initially located at the ulnar styloid process. Once the impedance probe is appropriately positioned the monitoring process is activated at step 430, typically using an appropriate input command provided to the measuring device 100, for example, via the I/O device 105.

At step 440 the measuring device 100 applies a current signal to the subject via the first electrodes 113, 114 and concurrently measures the voltage induced across the subject using the second electrode 115 and the probe 116. It will be appreciated that in practice the signal generator 111, and the sensor 112, return signals to the processing system 102 indicative of the applied current and the measured voltage, allowing impedances to be determined.

At step 450 the measuring device 100 will optionally determine positional information from the probe. This may be achieved for example by having either the position sensor 316, or signals from the detector 327 transferred to the measuring device 100 and interpreted appropriately.

At step 460 the measuring device 100 determines if the process is complete and if not returns to step 440 to allow further measurements to be performed.

It will be appreciated by persons skilled in the art that whilst this is being performed the operator will slide or roll the probe 116 along the dorsal skin surface towards the acromion, allowing an impedance profile of the entire limb to be determined. In one example, the probe is held stationery at the beginning and end points for 5 seconds to allow stable end point readings to be determined. In this example, the measurement of an impedance profile typically takes approximately 20 seconds, although this of course depends on the preferred implementation.

Once the probe has been positioned at the acromion, the user can select an appropriate input command utilising the I/O device 105, allowing the measuring device 100 to determine the process is complete at step 460.

At step 470 the measuring device 100 will determine appropriate impedance parameter values, using these to generate impedance profiles at step 480. The manner in which this is achieved will depend on the nature of the impedance measurements performed.

In the case of BIS analysis, the impedance profile can be based on impedance parameter values, such as values of the impedance at zero, characteristic or infinite frequencies ($R_0$, $Z_c$, $R_\infty$). These values can be derived based on the impedance response of the subject, which at a first level can be modelled using equation (1), commonly referred to as the Cole model:

$$Z = R_\infty + \frac{R_0 - R_\infty}{1 + (j\omega\tau)} \quad (1)$$

where: $R_\infty$=impedance at infinite applied frequency,
$R_0$=impedance at zero applied frequency,
$\omega$=angular frequency,
$\tau$ is the time constant of a capacitive circuit modelling the subject response.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \quad (2)$$

where: $\alpha$ has a value between 0 and 1 and can be thought of as an indicator of the deviation of a real system from the ideal model.

The value of the impedance parameters $R_0$ and $R_\infty$ may be determined in any one of a number of manners such as by:
solving simultaneous equations based on the impedance values determined at different frequencies;
using iterative mathematical techniques;
extrapolation from a "Wessel plot";
performing a function fitting technique, such as the use of a polynomial function.

Alternatively, in the case of a BIA analysis, the impedance profile is based on the actual measured impedance values, or parameters derived therefrom using suitable techniques.

It will be appreciated that whilst BIS analysis generally leads to an improved range of information, time constraints may limit its usage. For example, some examples measuring devices can take up to 800 msec to complete a frequency scan, in which case the probe may have to be moved at a rate that is too slow for practical purposes to prevent the probe moving a significant distance along the limb during a frequency scan. This in turn effects the usability of the process. Accordingly, in many cases it is preferred to perform measurements at a single selected frequency in the range 5 kHz to 1 MHz at a sampling rate of 1 reading per msec. Using this arrangement, with a twenty second measurement protocol allows 20,000 readings to be established along the length of the arm, thereby allowing a suitable profile to be established. It will be appreciated however that a greater or lesser number of measurements made be used depending for example on the intended use of the measurements.

Examples of derived profiles will now be described. For the purpose of this example, the profiles are compared to limb volumes, which are currently a preferred mechanism for determining the presence, absence or degree of oedema.

In this regard, the volume of a cylindrical body can be determined from measurements of its length and impedance according to the relationship:

$$\text{Vol} = \rho \frac{L^2}{Z} \quad (3)$$

where: L is length (cm),
Z is impedance (ohm); and,
$\rho$ is the resistivity constant (ohm.cm).

Since a short segment of a limb approximates a cylinder, if the impedance (Z) of the segment is measured then the volume of the limb segment can be estimated. The value of $\rho$ may be obtained from regression of the impedance quotient, $L^2/Z$, against limb volume, measured by a reference technique, such as DEXA (Dual Energy X-ray Absorptiometry), MRI (Magnetic Resonance Imaging), perometry, or the like, in an independent group of subjects.

Figure 6A:
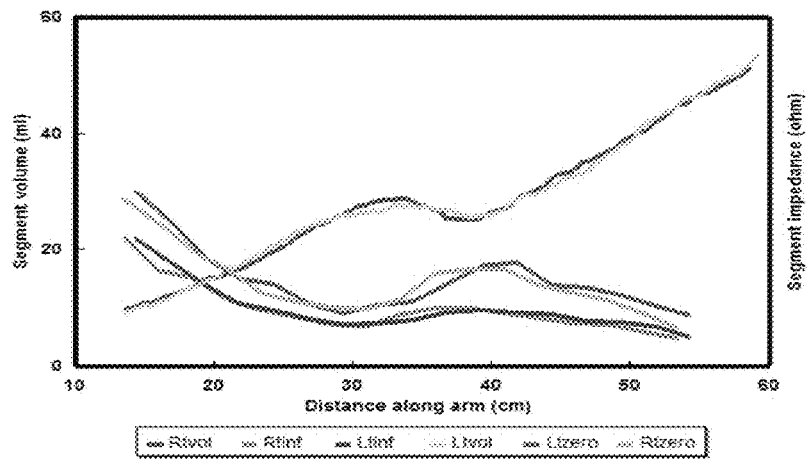
FIG. 6A is a graphical representation of an example of a profile of typical arm volume and impedance.

Example profiles are shown in FIG. 6A. This shows example impedance profiles, along both the left and right arms, of a number of test subjects. The figure presents the impedances at zero and infinite frequency calculated from BIS measurements for sequential 2.5 cm segments, as well as perometer volume measurements for equivalent segment volumes. In this example, in which measurements are collected for segments only, a limited number of readings can be collected using the probe, or alternatively, the probe could be replaced by a number of second electrodes positioned along the limb.

The impedance profile along the arm is the inverse of that seen for segment volume as expected from Equation (3), with a high correlation between the impedance and volume measurements being demonstrated. The position of the elbow, indicated by a change in volume and impedance is clearly discernable.

Figures 6B, 6C:
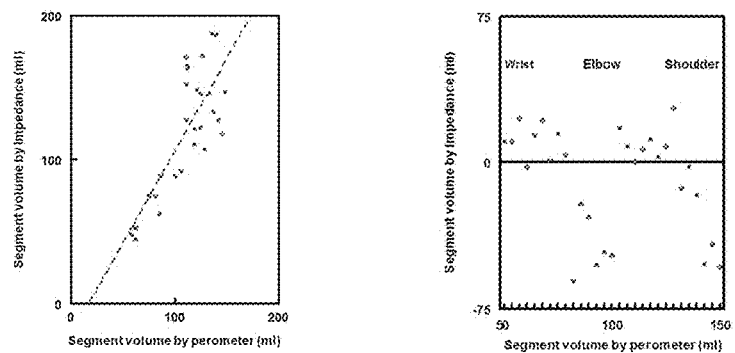
FIG. 6B is a graphical representation of an example of a correlation of arm segment volume measured using a perometer with that predicted by impedance.
FIG. 6C is a graphical representation of an example of limits of agreement between measured and predicted segment volumes.

FIG. 6B shows the correlation of arm segment volume measured by perometer with that predicted by impedance according to Equation (3). As shown, in FIG. 6C, limits of agreement between the two methods are variable depending upon the limb region being measured. For example, agreement was closest for the predominantly cylindrical regions of the forearm and biceps/triceps region and worse for the joint regions of the elbow and shoulder.

Figure 6D:
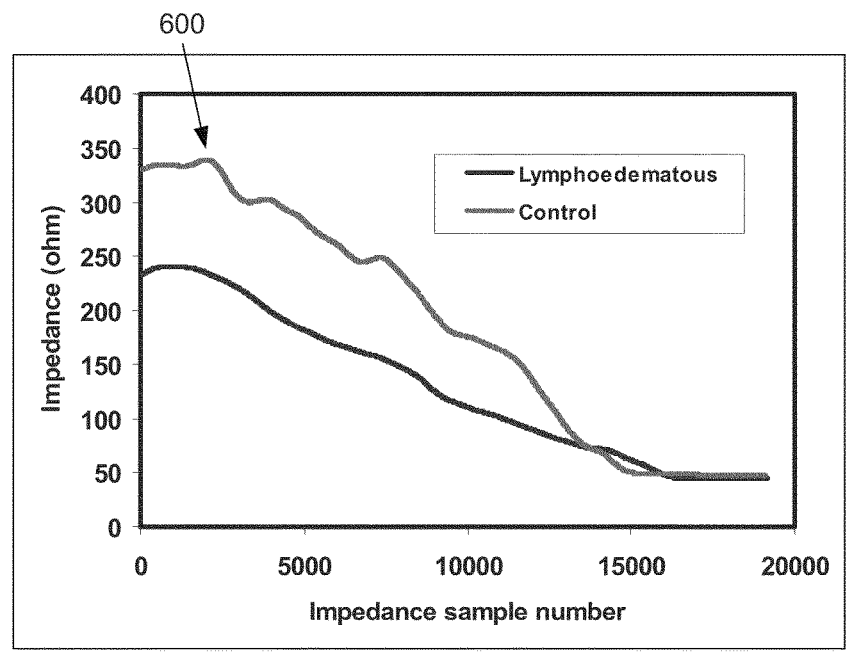
FIG. 6D is a graphical representation of an example of impedance profiles of an arm with lymphoedema and a contralateral unaffected arm; and,
FIG. 6E is a graphical representation of an example of cumulative limb volumes measured by perometry from wrist to shoulder.

An example of the impedance profile of the arms of a subject with unilateral lymphoedema is shown in FIG. 6D. As shown in this example, the impedance decreases as the electrode is moved from the wrist towards the shoulder reflecting the shortening inter-electrode distance between the second electrode 115 and the probe 116. Furthermore, the impedance is higher in the unaffected limb compared to that of the affected limb, highlighting the presence and magnitude of oedema.

It will be appreciated from this that when the measuring device 100 presents a measured impedance profile, it can include a reference or baseline measurement.

For example, a baseline is typically a previous impedance profile created from an impedance profile measurement that has significance in the treatment history of the subject. A common baseline in use might be an impedance profile measurement made on a patient suffering from lymphoedema before they start a course of management therapy. This measurement allows the practitioner to gauge accurately how much the patient has improved from the start of their treatment to the present measurement.

Baseline measurements may also be made pre-surgery and hence pre-lymphoedema, in which case the baseline impedance profile establishes the "normal" healthy impedance profile for the individual patient and can be used thereafter as a benchmark from which to monitor progress of the patient. Baselines can also be set using a single measurement or be created from the average of a number of measurements specified by the user.

The reference is typically formed from an impedance profile derived from a normal population (subject's not suffering from oedema) that is relevant to the subject under study. Thus, the normal population is typically selected taking into account factors such as medical interventions performed, ethnicity, sex, height, weight, limb dominance, the affected limb, or the like.

Therefore if the test subject has unilateral lymphoedema of the dominant arm and is female then the normalised data drawn from the normal population database will be calculated from the dominant arm measurements from female subjects that are present in the in the normal population database.

Accordingly, at this stage the processing system 102 typically accesses reference populations stored in the database, or the like. This may be performed automatically by the processing system 102 using the subject details. Thus for example, the database may include a look-up table that specifies the normal population that should be used given a particular set of subject details. Alternatively selection may be achieved in accordance with predetermined rules that can be derived using heuristic algorithms based on selections made by medically qualified operators during previous procedures. Alternatively, this may achieved under control of the operator, depending on the preferred implementation.

Operators may also have their own reference normal populations stored locally. However, in the event that suitable populations are not available, the processing system 102 can be used to retrieve a reference from a central repository, for example via an appropriate server arrangement. In one example, this may be performed on a pay per use basis.

The reference may also need to be scaled to take into account differing limb lengths of subjects measured, which can be determined from probe positional information if this is present.

In this instance, the measured impedance profile can be displayed concurrently with reference impedance profiles representing healthy limbs and representing subjects with oedema, to thereby highlight to the operator whether oedema is likely, and if so, where on the limb this has occurred, or is most severe.

Additionally, and/or alternatively, in the case of unilateral oedema, impedance profiles can be displayed for each limb, thereby allowing comparison between contra-lateral limbs. Thus, in this example, the impedance profile of a healthy limb acts as a baseline or reference against which the profile of the affected limb can be compared.

Display of the representation may be achieved in a number of ways, such as by presenting the representation on a suitable display, for example, using the I/O device 105, or alternatively by providing the representation in a hard copy form using an appropriate printer, although any suitable technique may be used.

Figure 6E:
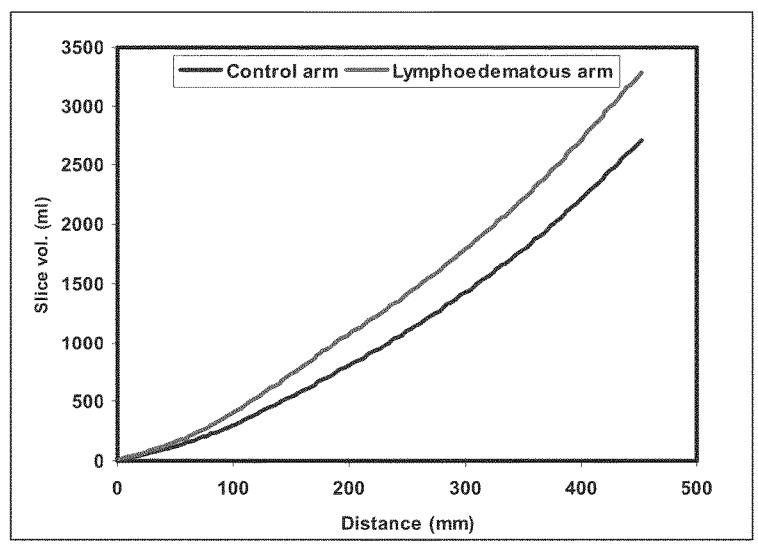

An example of comparable cumulative volume measurements are shown in FIG. 6E, highlighting that the magnitude difference obtained between arms is greater for the impedance measurements (FIG. 6D) than the equivalent volume measurements (FIG. 6E).

Furthermore, as impedance analysis in the above described manner can be used to focus on the levels of extracellular fluid in the limb, this tends to provide a more accurate assessment of fluid distributions within the limb than volume measurements alone.

In particular, it can be seen that whilst the volumetric measurements in FIG. 6E present a smooth curve, implying there is a relatively equal distribution of fluid along the limb, the impedance profiles of FIG. 6D include a number of bumps and troughs, particularly in the lymphoedematous limb. Thus, the impedance profile of FIG. 6D indicates not only that there is a difference in fluid levels between the limbs, and hence that there is the presence of lymphoedema, but also can be used to determine in which area of the arm fluid concentrations are highest and/or lowest, thereby allowing highly localised oedema to be diagnosed.

In the example of FIG. 6D, it can be seen that there is a significant peak shown at 600 which was obtained near the start of the reading cycle. This suggests that a segment in the arm near the wrist has a high fluid level thereby indicative of lymphoedema. It is also noticeable that towards the end of the profile the readings are similar to the readings for the control arm and hence that the lymphoedema is prevalent primarily in the lower limb.

Accordingly, by correlating the impedance measurements with the distance traveled along the arm or other limb it is possible not only to detect that the limb is lymphoedematous but also the particular location of lymphoedema within the limb thereby rendering it easier to detect the presence, absence, degree or location of oedema using impedance profiling than volumetric measurements.

In the above described examples, impedance measurements along the limb or other body segment are achieved by moving a probe along the respective body segment. However, this is not essential, and as an alternative, a sequence of second electrodes may be placed along the subject's limb, to allow impedance measurements to be recorded at a number of different locations along the limb.

Whilst the electrodes can be standard electrodes, positioned as required by the operator, an alternative electrode configuration suitable for performing this will now be described with reference to FIGS. 7A to 7F.

In this particular example the electrode is a band electrode 700, which includes a number of separate electrodes. In this example the electrode is formed from an elongate substrate 710 such as a plastic polymer coated with shielding material and an overlaying insulating material.

A number of electrically conductive tracks 720 are provided on the substrate extending from an end of the substrate 711 to respective conductive contact pads 730, spaced apart along the length of the substrate in sequence. This allows a connector to be electrically coupled to the tracks 720 and provide onward connectivity to leads, such as leads 126.

The tracks 720 and the contact pads 730 may be provided on the substrate 710 in any one of a number of manners, including for example, screen printing, inkjet printing, vapour deposition, or the like, and are typically formed from silver or another similar material. It will be appreciated however that the tracks and contact pads should be formed from similar materials to prevent signal drift. Furthermore, whilst circular contact pads 730 are shown, in practice these could be of any suitable shape.

Following the application of the contact pads 730 and the tracks 720, an insulating layer 740 is provided having a number of apertures 750 aligned with the electrode contact pads 730. The insulating layer is typically formed from a plastic polymer coated with shielding material and an overlaying insulating material.

To ensure adequate conduction between the contact pads 730, and the subject S, it is typical to apply a conductive gel 760 to the contact pads 730. It will be appreciated that in this instance gel can be provided into each of the apertures 750 as shown.

A removable covering 770 is then applied to the electrode, to maintain the electrode's sterility and/or moisture level in the gel. This may be in the form of a peel off strip or the like which when removed exposes the conductive gel 760, allowing the electrode to be attached to the subject S.

In order to ensure signal quality, it is typical for each of the tracks 720 to comprise a shield track 721, and a signal track 722, as shown. This allows a shield on the leads 126 to be connected to the shield track 721, with the lead core being coupled to the signal track 722. This allows shielding to be provided on the electrode, to help reduce interference between applied and measured signals.

Figure 7A:
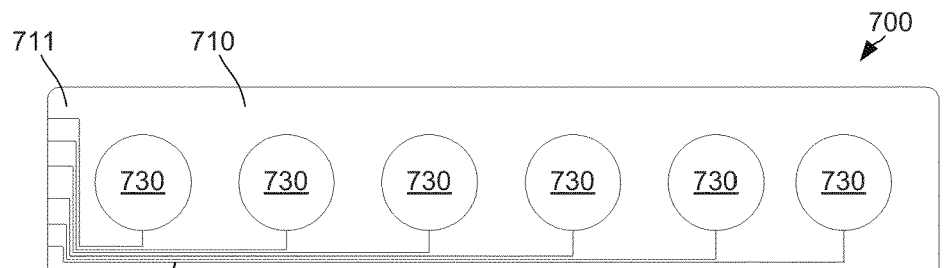
FIGS. 7A to 7F are schematic diagrams of an example of the construction of a band electrode.
Figure 7B:
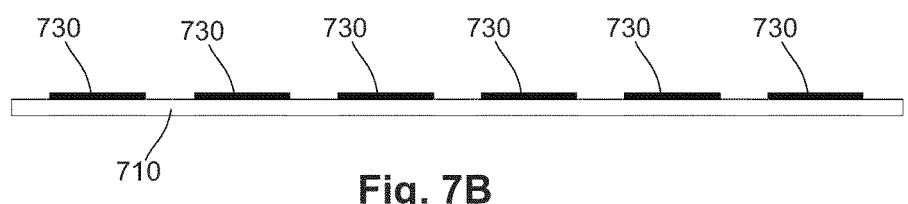
Figure 7C:
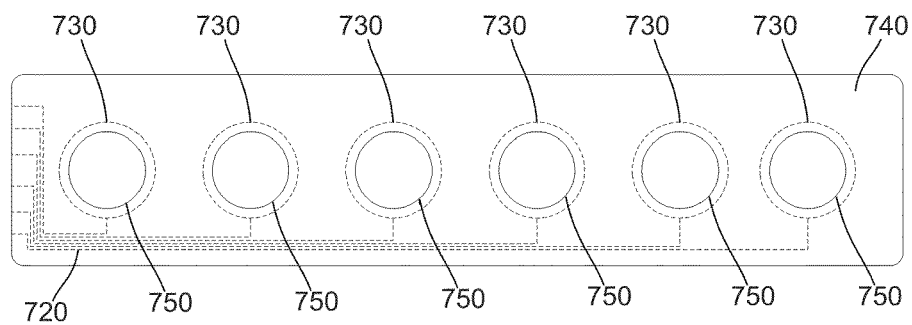
Figure 7D:
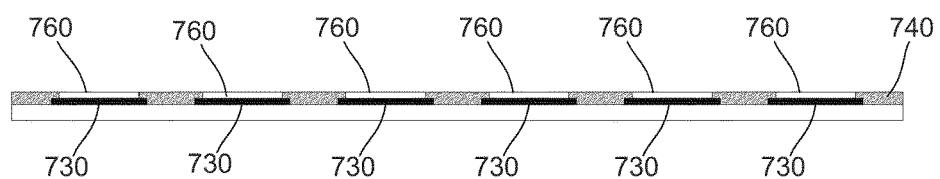
Figure 7E:
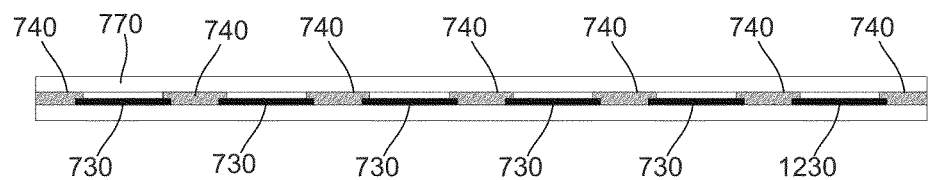
Figure 7F:
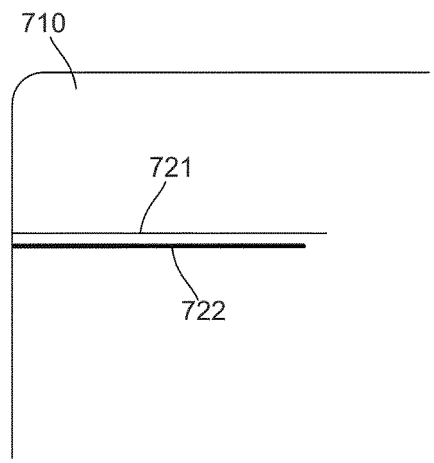
Figure 7G:
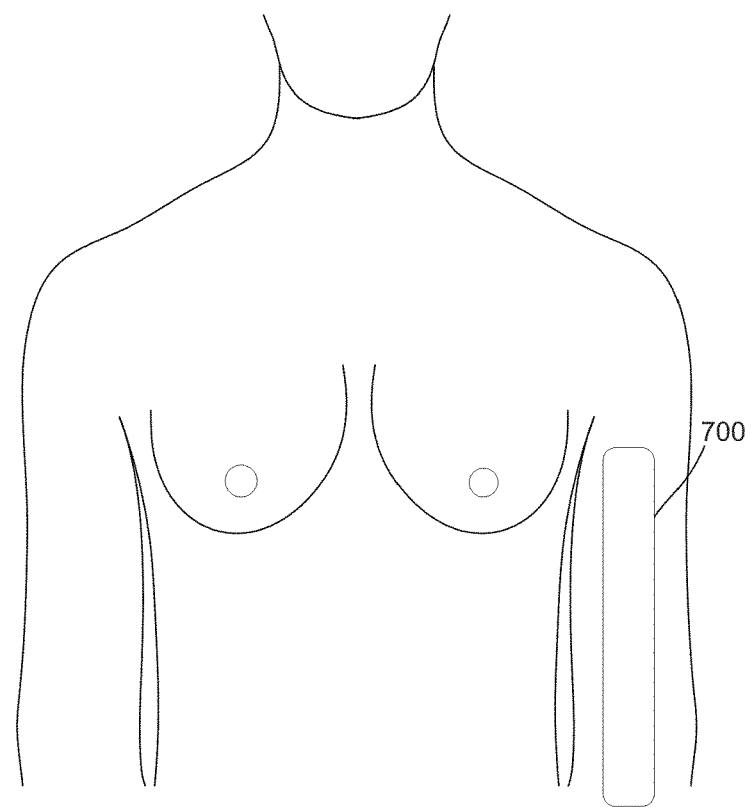
FIG. 7G is a schematic diagram of the use of a band electrode.

In use, the band electrode may be attached to a limb segment of the subject, such as the subject's arm, as shown in FIG. 7G. The electrode will typically include an adhesive surface, allowing it to stick to the subject. This provides an electrode that is easy to attach and position on the subject, and yet can be worn for an extended period if necessary. The band electrode 700 may also be positioned on the subject at other locations, such as on the side of the subject's torso, or laterally above the naval, on the leg, or the like.

Once positioned, the band electrode can be connected to the switching device 118 via respective leads 126, with a separate lead being provided for each contact pad 730. In this instance, it will be appreciated that in this instance, the measuring device 100 can control the switching device 118 so that readings are taken from each of the contact pads 730 in turn. This allows readings along the entire body segment to be taken automatically by the measuring device 100, without requiring operator intervention, for example, by requiring the operator move the probe 116 along the subject's body segment.

In one example, the band electrode 700 provides sufficient electrodes to allow an impedance profile to be measured. In the above example, the band electrode includes six electrodes, however any suitable number may be used depending on the preferred implementation.

It will be appreciated that the use of a band electrode will generally not allow as great a resolution to be achieved as compared to the use of the probe described above, simply as readings can only be sampled at each of the contact pad locations, as opposed to continuous sampling along the length of the limb. However, the use of a band electrode does have some advantages.

Firstly, the contact pads are provided at definite positions on the band electrode, thereby allowing for easy and accurate determination of the position at which each impedance measurement is made.

Secondly, as the contact pads can be held in position for a longer period of time, this makes the band electrode particularly suited for performing BIS analysis over a large number of frequencies, in which readings at each position may take some time.

It will also be appreciated that as an alternative to using a band electrode, separate discrete electrodes may be positioned along the length of the limb.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used for determining the health status of an individual, including the body composition of the individual, or diagnosing the presence, absence or degree of a range of conditions and illnesses, including, but not limited to oedema, lymphoedema, or the like. It will be appreciated from this that whilst the above examples use the term impedance profile, this is for the purpose of example only and is not intended to be limiting. Accordingly, the impedance profile can be referred to more generally as an indicator when used in analysing impedance measurements with respect to more general health status information such as body composition, or the like.

The claims defining the invention are as follows:

1. An apparatus comprising:
   a signal generator;
   a sensor;
   a pair of first electrodes coupled to the signal generator, the pair of first electrodes independently positionable on different limbs of a subject; and
   a pair of second electrodes coupled to the sensor, the pair of second electrodes positionable on different limbs of the subject,
   wherein the pair of second electrodes includes a probe for use in performing impedance measurements on a subject, the probe comprising:
   a) a housing configured to be held by an operator in use;
   b) a contact surface for contacting the subject, wherein the contact surface includes a moving member for moving relative to the subject, and wherein the moving member is movably mounted to the housing and is configured to roll within the housing and along a tissue surface of the subject;
   c) a connector for connecting the contact surface to the apparatus; and,
   d) a position sensor for sensing movement of the moving member, wherein the position sensor is configured to transmit information indicative of the position of the probe; and
   wherein, in use, the probe is moved along a segment of the subject to thereby allow an impedance profile representing variations in impedance along the segment to be determined.

2. The apparatus according to claim 1, wherein the housing is an elongate housing, the contact surf ace is provided at a first end of the housing and the connector is provided at a second opposing end of the housing.

3. The apparatus according to claim 1, wherein the housing is formed from an insulating material.

4. The apparatus according to claim 1, wherein the housing is formed from a poly(methyl) methacrylate tube.

5. The apparatus according to claim 1, wherein the contact surface has a convex shape.

6. The apparatus according to claim 1, wherein the moving member is a roller ball, and wherein the housing includes a shaped mounting for receiving the roller ball.

7. The apparatus according to claim 1, wherein the moving member is a cylindrical roller mounted on an axle.

8. The apparatus according to claim 1, wherein the probe includes a contact for electrically connecting the moving member to the connecter.

9. The apparatus according to claim 8, wherein the contact is a spring.

10. The apparatus according to claim 1, wherein the position sensor for sensing movement of the moving member includes at least one of:
    a) an optical sensor; and
    b) moving elements in contact with the moving member.

11. The apparatus according to claim 1, wherein the connector is for connecting to a lead of the apparatus.

12. The apparatus according to claim 1, wherein, in use, the probe is connected to a processing system for:
    a) causing at least one electrical signal to be applied to the subject via the pair of first electrodes provided on the subject; and
    b) determining an indication indicative of at least one second electrical signal measured via the second pair of electrodes positioned on the subject including via the probe.

13. A method of performing impedance measurements on a subject using an apparatus, the apparatus comprising:
    a signal generator;
    a sensor;
    a pair of first electrodes coupled to the signal generator, the pair of first electrodes independently positionable on different limbs of a subject; and
    a pair of second electrodes coupled to the sensor, the pair of second electrodes positionable on different limbs of the subject,
    wherein the pair of second electrodes includes a probe comprising a housing configured to be held by an operator in use, a contact surf ace for contacting the subject wherein the contact surface includes a moving member for moving relative to the subject and wherein the moving member is movably mounted to the housing and is configured to roll within the housing and along a tissue surface of the subject, a connector for connecting the contact surface to the apparatus, and a position sensor for sensing movement of the moving member wherein the position sensor is configured to sense rolling motion of the moving member with respect to the housing,
    the method, comprising:
    a) positioning the probe in contact with a segment of the subject, the segment being on a limb of the subject;
    b) causing the apparatus to perform a sequence of impedance measurements; and
    c) moving the probe along the segment during the sequence of impedance measurements so that the apparatus:
       i) determines positional information along different positions on the segment using the position sensor;
       ii) determines impedance measurements along different positions on the segment, at least some of the impedance measurements correlated with positional information; and
       iii) uses the impedance measurements to determine an impedance profile.

14. The method according to claim 13, wherein the method further includes displaying a representation of the impedance profile to thereby allow the impedance profile to be used in determining a presence, absence, degree or location of oedema in the subject.

15. The method according to claim 13, wherein the method includes:
    a) causing a sequence of first electrical signals to be applied to the subject via the pair of first electrodes provided on the subject connected to the signal generator; and
    b) determining an indication of a sequence of second electrical signals measured via the pair of second electrodes positioned on the subject including via the probe.

16. The method according to claim 15, wherein the method includes: using an indication of the first and second signals to determine the impedance profile, the impedance profile representing variations in measured impedance along the segment.

17. The apparatus according to claim 1, wherein the probe is for use in diagnosing oedema in a body segment of the subject.

18. A method of diagnosing oedema in a body segment of a subject using a measuring device, the measuring device comprising:
    a signal generator;
    a sensor;

a pair of first electrodes coupled to the signal generator, the pair of first electrodes independently positionable on different limbs of a subject; and a pair of second electrodes coupled to the sensor, the palf of second electrodes positionable on different limbs of the subject, wherein the pair of second electrodes includes a probe, the probe comprising a housing configured to be held by an operator in use, a contact surface for contacting the subject wherein the contact surface includes a moving member for moving relative to the subject and wherein the moving member is movably mounted to the housing and is configured to roll within the housing and along a tissue surf ace of the subject, a connector for connecting the contact surf ace to the measuring device, and a position sensor for sensing movement of the moving member wherein the position sensor is configured to sense rolling motion of the moving member with respect to the housing, the method comprising:
a) positioning the probe in contact with a segment of the subject, the segment being on a limb of the subject;
b) causing the measuring device to perform a sequence of impedance measurements;
c) moving the probe along the segment during the sequence of impedance measurements sothat the measuring device:
 i) determines positional information along the segment using the position sensor; and,
 ii) determines impedance measurements along the segment; and
d) determining an impedance profile using the sequence of impedance values and the positional information, the impedance profile being indicative of a presence, absence, degree or location of oedema in the subject.

19. An apparatus for use in performing impedance measurements on a
subject, the apparatus comprising:
a) a probe including:
 i) a housing configured to be held by an operator in use;
 ii) a contact surface for contacting the subject, wherein the contact surface includes a moving member for moving relative to the subject, and wherein the moving member is movably mounted to the housing and is configured to roll within the housing and along a tissue surf ace of the subject;
 iii) a connector for connecting the contact surface to a measuring device; and,
 iv) a positional sensor for sensing movement of the moving member, wherein the position sensor is configured to sense rolling motion of the moving member with respect to the housing,
b) a measuring device including a processing system for performing a sequence of impedance measurements as the probe is moved along a segment of the subject, so that the measuring device determines positional information along the segment using the position sensor, and determines impedance measurements along the segment and uses the impedance measurements and positional information to determine an impedance profile, the impedance profile representing variations in measured impedance along the segment.

20. The apparatus according to claim 19, wherein the housing is an elongate housing, the contact surf ace is provided at a first end of the housing and the connector is provided at a second opposing end of the housing.

21. The apparatus according to claim 19, wherein the housing is formed from an insulating material.

22. The apparatus according to claim 19, wherein the housing is formed from a poly(methyl) methacrylate tube.

23. The apparatus according to claim 19, wherein the contact surface has a convex shape.

24. The apparatus according to claim 19, wherein the moving member is a roller ball, and wherein the housing includes a shaped mounting for receiving the roller ball.

25. The apparatus according to claim 19, wherein the moving member is a cylindrical roller mounted on an axle.

26. The apparatus according to claim 19, wherein the probe includes a contact for electrically connecting the moving member to the connecter.

27. The apparatus according to claim 26, wherein the contact is a spring.

28. The apparatus according to claim 19, wherein the position sensor for sensing movement of the moving member includes at least one of:
a) an optical sensor; and,
b) moving elements in contact with the moving member.

29. The apparatus according to claim 19, wherein the connector is for connecting to a lead of the measuring device.

30. A method of performing impedance measurements on a subject using an apparatus comprising:
a) a probe including:
 i) a housing configured to be held by an operator in use;
 ii) a contact surface for contacting the subject, wherein the contact surface includes a moving member for moving relative to the subject, and wherein the moving member is movably mounted to the housing and is configured to roll within the housing and along a tissue surf ace of the subject;
 iii) a connector for connecting the contact surface to a measuring device; and,
 iv) a position sensor for sensing movement of the moving member, wherein the position sensor is configured to sense rolling motion of the moving member with respect to the housing,
b) a measuring device including a processing system, the method including:
 i) positioning the probe in contact with a segment of the subject;
 ii) causing a measuring device to perform a sequence of impedance measurements;
 iii) moving the probe along the segment during the sequence of impedance measurements so that the measuring device determines impedance measurements along the segment and the position sensor senses motion of the moving member;
 iv) determining positional information using the position sensor; and
 v) using the impedance measurements and positional information to determine an impedance profile, the impedance profile representing variations in measured impedance along the segment.

31. A method according to claim 30, wherein the method includes, in the measuring device, displaying a representation of the impedance profile to thereby allow the impedance profile to be used in determining a presence, absence, degree or location of oedema in the subject.

32. A method according to claim 30, wherein the method includes, in the measuring device:
a) causing a sequence of first electrical signals to be applied to the subject via first electrodes provided on the subject; and, b) determining an indication of a sequence of second electrical signals measured via a second electrode positioned on the subject, and via the probe.

33. A method according to claim 32, wherein the method includes, in the measuring device, using an indication of the first and second signals to determine the impedance profile.

34. A method according to claim 32, wherein the method includes in the processing system:
   a) causing a sequence of first signals to be applied to the subject via first electrodes provided on the subject;
   b) determining an indication indicative of a sequence of second electrical signals measured via second electrodes provided on the subject; and,
   c) determining the sequence of impedance values using indications of the sequences of first and second signals.

35. A method according to claim 34, wherein one of the second electrodes is a probe, and wherein the method includes determining an indication of at least some of the second electrical signals as the probe is moved along the segment.

36. A method according to claim 30, wherein the method includes, in the processing system:
   a) determining one or more impedance parameter values from measured impedance values; and,
   b) determining the impedance profile using the impedance parameter values.

37. A method according to claim 36, wherein the impedance parameter values include at least one of:
   a) an impedance at infinite applied frequency (Ref;));
   b) an impedance at zero applied frequency (R0); and,
   c) an impedance at a characteristic frequency (Zc).

38. A method according to claim 37, wherein the method includes, in the processing system, determining the impedance parameter values at least in part using the equation:

$$Z = R_\infty + \frac{R_0 - R_\infty}{1 + (j\omega\tau)^{(1-\alpha)}}$$

where: R∞=impedance at infinite applied frequency;
Ro=impedance at zero applied frequency;
ω=angular frequency;
τ is the time constant of a capacitive circuit modelling the subject response; and,
α has a value between 0 and 1.

39. A method according to claim 31, wherein the representation includes at least one of:
   a) a baseline impedance profile for the segment;
   b) a reference impedance profile derived from a normal population; and,
   c) an impedance profile for a contra-lateral segment.

40. A method according to claim 39, wherein the method includes, in the processing system:
   a) determining one or more subject details; and,
   b) selecting a reference at least partially in accordance with the subject details.

41. A method according to claim 40, wherein the subject details include at least one of:
   a) limb dominance;
   b) ethnicity;
   c) age;
   d) sex;
   e) weight; and,
   f) height.

42. An apparatus for use in diagnosing oedema in a body segment of a subject, the apparatus comprising:
   a) a probe including:
      i) a housing configured to be held by an operator in use;
      ii) a contact surface for contacting the subject, wherein the contact surface includes a moving member for moving relative to the subject, and wherein the moving member is movably mounted to the housing and is configured to roll within the housing and along a tissue surf ace of the subject;
      iii) a connector for connecting the contact surface to a measuring device; and,
      iv) a position sensor for sensing movement of the moving member, wherein the position sensor is configured to sense rolling motion of the moving member with respect to the housing,
   b) a measuring device including a processing system for performing a sequence of impedance measurements as the probe is moved along a segment of the subject, so that the measuring device determines positional information along the segment using the position sensor, determines impedance measurements along the segment and uses the impedance measurements and positional information to determine an impedance profile, the impedance profile representing variations in measured impedance along the segment.

43. A method of diagnosing oedema in a body segment of a subject using apparatus comprising:
   a) a probe including:
      i) a housing configured to be held by an operator in use;
      ii) a contact surface for contacting the subject, wherein the contact surface includes a moving member for moving relative to the subject, and wherein the moving member is movably mounted to the housing and is configured to roll within the housing and along a tissue surf ace of the subject;
      iii) a connector for connecting the contact surface to a measuring device; and,
      iv) a position sensor for sensing movement of the moving member, wherein the position sensor is configured to sense rolling motion of the moving member with respect to the housing,
   b) a measuring device including a processing system, the method including:
      i) positioning the probe in contact with a segment of the subject;
      ii) causing a measuring device to perform a sequence of impedance measurements;
      iii) moving the probe along the segment during the sequence of impedance measurements so that the measuring device determines impedance measurements along the segment and the position sensor senses motion of the moving member
      iv) determining positional information using the position sensor; and
      v) using the impedance measurements and positional information to determine an impedance profile, the impedance profile being indicative of a presence, absence, degree or location of oedema in the subject.

* * * * *